United States Patent [19]

Cianciolo

[11] Patent Number: 5,268,455
[45] Date of Patent: Dec. 7, 1993

[54] PROCESS FOR MAKING BIOLOGICALLY ACTIVE POLYPEPTIDES BASED ON TRANSFORMING GROWTH FACTOR-βSEQUENCES

[75] Inventor: George J. Cianciolo, San Carlos, Calif.

[73] Assignee: Genentech, Inc., South San Francisco, Calif.

[21] Appl. No.: 824,622

[22] Filed: Jan. 23, 1992

Related U.S. Application Data

[62] Division of Ser. No. 714,462, Jun. 13, 1991, Pat. No. 5,118,791, which is a division of Ser. No. 356,964, May 25, 1989, Pat. No. 5,061,786.

[51] Int. Cl.$^5$ .................... C07K 7/08; A61K 37/02
[52] U.S. Cl. .................... 530/404; 530/300; 530/324; 530/326
[58] Field of Search ............. 424/85.1; 530/326, 300, 530/324, 403, 404

[56] References Cited

U.S. PATENT DOCUMENTS

| | | | |
|---|---|---|---|
| 4,774,228 | 9/1988 | Seyedin et al. | 530/324 |
| 4,774,322 | 9/1988 | Seyedin et al. | 530/324 |
| 4,806,523 | 2/1989 | Bentz et al. | 514/2 |
| 4,810,691 | 3/1989 | Seyedin et al. | 530/324 |
| 4,816,442 | 3/1989 | McPherson et al. | 530/324 |
| 4,816,449 | 3/1989 | Hahn | 514/17 |
| 4,822,606 | 4/1989 | Snyderman et al. | 424/88 |
| 4,843,063 | 6/1989 | Seyedin et al. | 530/324 |
| 4,931,548 | 6/1990 | Lucas et al. | 530/324 |

FOREIGN PATENT DOCUMENTS

| | | |
|---|---|---|
| 0169016 | 1/1986 | European Pat. Off. |
| 0267463 | 5/1988 | European Pat. Off. |
| 0269408 | 6/1988 | European Pat. Off. |
| 0271211 | 6/1988 | European Pat. Off. |
| 290012 | 11/1988 | European Pat. Off. |
| WO8805783 | 8/1988 | PCT Int'l Appl. |
| WO8805788 | 8/1988 | PCT Int'l Appl. |

OTHER PUBLICATIONS

Atassi, Immunochemistry of proteins, vol. 1, pp. 94–102, Plenum Press, 1977.
Qian et al. CA 113–166461c (1990).
Purchio et al., CA 113–206226p (1990).
Purchio et al., CA 111–18827v (1989).
Lucas et al., CA 111–91268q (1989).
Espevik et al., *J. Exp. Med.*, 166: 571–576 (1987).
Kehrl et al., *J. Exp. Med.*, 163: 1036–1050 (1986).
Ristow et al., *Proc. Natl. Acad. Sci.*, USA, 83: 5531 (1986).
Ranges et al, *Immunobiology*, 175:42 (1987).
Schmidt et al., *Proc. Natl. Acad. Sci.*, USA, 84: 7290–7294 (1987).
Rook, et al. *J. Immunol.*, 136: 3916 (1986).

*Primary Examiner*—David L. Lacey
*Assistant Examiner*—Ron Schwadron
*Attorney, Agent, or Firm*—Janet E. Hasak

[57] ABSTRACT

A polypeptide is provided that excludes (a) a full-length mature TGF-β molecule or precursor TGF-β molecule or deletion variants of mature or precursor TGF-β molecules in which from about 1 to 10 amino acid residues have been deleted, (b) a polypeptide of the sequence: Cys-Val-Arg-Gln-Leu-Tyr-Ile-Asp-Phe-Arg-Lys-Asp-Leu-Gly-Trp-Lys, and (c) a polypeptide of the sequence: Arg-Asn-Leu-Glu-Glu-Asn-Cys-Cys-Val-Arg-Pro-Leu-Tyr-Ile-Asp-Phe-Arg-Gln-Asp-Leu, the polypeptide comprising an amino acid sequence that is based on conserved sequences in the family of TGF-β molecules. Such polypeptides are particularly useful therapeutically as immunosuppressive agents when coupled to carrier proteins or crosslinked to form polymers.

**10 Claims, 7 Draw

FIG. I

PROCESS FOR MAKING BIOLOGICALLY ACTIVE POLYPEPTIDES BASED ON TRANSFORMING GROWTH FACTOR-βSEQUENCES

This is a divisional of copending application Ser. No. 07/714,462 filed on Jun. 13, 1991, now U.S. Pat. No. 5,118,791, which is a divisional of application Ser. No. 07/356,964 filed on May 25, 1989, now U.S. Pat. No. 5,061,786.

This application is related to copending U.S. application Ser. No. 07/356,965 filed on May 25, 1989, now abandoned, entitled "Biologically Active Polypeptide Monomer Based on Transforming Growth Factor-Beta Sequences," and to copending U.S. application Ser. No. 07/356,963 filed on May 25, 1989, now abandoned, entitled "Nucleic Acid Encoding TGF-β Variants and Their Uses."

BACKGROUND OF THE INVENTION

1. Field of the Invention

This invention relates to biologically active polypeptides based on transforming growth factor-beta sequences that have transforming growth factor-betalike activity. In particular, this invention relates to the development of drugs for treatment of immune or inflammatory disorders, such as allograft rejection, arthritis, cancer, and viral infections, and to immunodiagnostic reagents.

2. Description of Related Art

The transforming growth factor-β (TGF-β) molecules identified thus far are each dimers containing two identical 112 residue polypeptide chains linked by disulfide bonds. The molecular mass of these dimers is about 25 kd. Biologically active TGF-β has been defined as a molecule capable of inducing anchorage independent growth of target cell lines or rat fibroblasts in in vitro cell culture, when added together with EGF or TGF-α as a co-factor. TGF-β is secreted by virtually all call types in an inactive form. This latent form can be activated by proteolytic cleavage of mature TGF-β from its precursor (at the Arg-Ala bond in position 278). A non-covalent complex is formed from the association of the mature TGF-β with the precursor remainder or with a protein binding to TGF-β or with alpha2-macroglobulin. This complex is disrupted so as to activate the TGF-β either by exposure to transient acidification or by the action of exogenous proteases such as plasmin or plasminogen activator.

There are at least three forms of TGF-β currently identified, TGF-$\beta_1$, TGF-$\beta_2$, and TGF-$\beta_3$. Suitable methods are known for purifying this family of TGF-βs from various species such as human, mouse, green monkey, pig, bovine, and chick, and from various body sources such as bone, platelets, or placenta, for producing it in recombinant cell culture, and for determining its activity. See, for example, R. Derynck et al., *Nature*, 316:701-705 (1985); U.S. Ser. Nos. 715,142; 500,832; 500,833, all abandoned; European Pat. Pub. Nos. 200,341 published Dec. 10, 1986, 169,016 published Jan. 22, 1986, 268,561 published May 25, 1988, and 267,463 published May 18, 1988; G.B. Pat. Appln. 2,146,335 published Apr. 17, 1985; U.S. Pat. No. 4,774,322; Seyedin et al, *J. Biol, Chem.*, 262:1946-1949 (1987); Cheifetz et al. *Cell*, 48: 409-415 (1987); Jakowlew et al., *Molecular Endocrin*, 2:747-755 (1988); Dijke et al., *Proc. Natl. Acad. Sci. (U.S.A.)*, 85:4715-4719 (1988); Derynck et al., *J. Biol, Chem.*, 261:4377-4379 (1986); Sharples et al., *DNA*, 6:239-244 (1987); Derynek et al., *Nucl. Acids. Res.*, 15:3188-3189 (1987); Derynck et al., *Nucl. Acids. Res.* 15:3187 (1987); Seyedin et al., *J. Biol, Chem.*, 261:5693-5695 (1986); Jakowlew et al., *Mol. Endrocrin.*, 2:1186-1195 (1988); Madisen at al., *DNA*, 7:1-8 (1988); and Hanks et al., *Proc. Natl. Acad. Sci. (U.S.A.)*, 85:79-82 (1988), the entire contents of these publications being expressly incorporated by reference.

TGF-β has been shown to have numerous regulatory actions on a wide variety of both normal and neoplastic cells. Recent studies indicate an important role for TGF-β in cells of the immune system (J. Kehrl et al., *J. Exp. Med.*, 163:1037 [1986]; H-J. Ristow, *Proc. Natl. Acad. Sci.* U.S.A., 11:5531 [1986]; A. Rook at al., *J. Immunol.*, 136:3916[1986]) and in proliferation of connective and soft tissue for wound healing applications (M. Sporn et al., *Science*, 219:1329 [1983]; R. Ignotz et al., *J. Biol. Chem.*, 261:4337 [1986]; J. Varga et al., *B.B.Res.Comm.*, 138:974 [1986]; A. Roberts et al., *Proc. Natl. Acad. Sci.* U.S.A., 21:5339 [1981]; A. Roberts et al., Fed. Proc., 42:2621 [1983]; A. Roberts et al., *Proc. Natl. Acad. Sci.* U.S.A., 12:4167 [1986]; U.S. Ser. No. 500,833, supra; U.S. Pat. No. 4,774,228 to Seyedin et al.), as well as epithelia (T. Matsui et al., *Proc, Nail. Acad. Sci.* U.S.A., 83:2438 [1986]; C. Shipley et al. *Cancer Res.*, 46:2068 [1986]). Moreover, TGF-β has been described as a suppressor of cytokine (e.g., IFN-γ, TNF-α) production, indicating its use as an immunosuppressant for treating inflammatory disorders (Espevik et al., *J. Exp. Med.*, 166:571-576 [1987]; European Pat. Pub. No. 269,408 published Jun. 1, 1988; U.S. Pat. No. 4,806,523 issued Feb. 21, 1989), and as a promoter of cachexia (Beutler and Cerami, *New Eng. J. Med.*, 316:379 [1987]). Further, TGF-β induces collagen secretion in human fibroblast cultures (Roberts et al., *Proc. Nat. Acad. Sci.* USA 83:4167-4171 (1986); Chua et al., *J. Biol, Chem.* 260:5213-5216 [1983]); stimulates the release of prostaglandins and mobilization of calcium (A. Tashjian et al., *Proc. Natl. Acad. Sci.* U.S.A., 82:4535 [1985]); and inhibits endothelial regeneration (R. Heimark et al., *Science*, 233:1078 [1986]).

TGF-β is multifunctional, as it can either stimulate or inhibit cell proliferation, differentiation, and other critical processes in cell function (M. Sporn, *Science*, 233:532 [1986]).

The multifunctional activity of TGF-β is modulated by the influence of other growth factors present together with the TGF-β. TGF-β can function as either an inhibitor or an enhancer of anchorage-independent growth, depending on the particular set of growth factors, e.g., EGF or TGF-α, operant in the cell together with TGF-β (Roberts et al., *Proc. Natl. Acad. Sci.* U.S.A., 12:119 [1985]). TGF-β also can act in concert with EGF to cause proliferation and piling up of normal (but not rheumatoid) synovial cells (Brinkerhoff et al., *Arthritis and Rheumatism*, 26:1370 [1983]).

Most recently, TGF-β has been found to suppress the expression of Class II histocompatibility antigens on human cells induced by human interferon-γ (Czarniecki et al., *J. Immunol.*, 140: 4217-42223 [1988]; Czarniecki et al. *J. Interferon Res.*, 7:699 [1987]; Palladino et al., *J. Cell, Biochem.*, Supp. 11A [Jan. 17-Feb. 5, 1987), UCLA Symposia on Molecular and Cellular Biology, Alan R. Liss, Inc., New York, abstract A016, p. 10; Chill et al., Triennial Symposium: Biology of Growth Factors, University of Toronto, Ontario, Canada, [Jun. 17-19, 1987]; Palladino et al., *Immunobiology*, 175:42 [1987]).

For a general review of TGF-β and its actions, see Sporn et al., *J. Cell Biol.*, 105:1039–1045 (1987) and Sporn and Roberts, *Nature*, 332:217–219 (1988).

Fragments of TGF-β are described in EP 290,012 published Nov. 9, 1988 and EP 267,463 published May 18, 1988. The former describes fragments of TGF-β2 having at least about eight amino acids, for example, in the region of N-terminal amino acids 1 to 20, particularly 4–15, and more particularly 9–14, a C-terminal sequence, or a truncated N-terminal or C-terminal molecule. The latter patent publication describes in claim 36 a 20-mer consisting of an internal sequence of TGF-β3.

TGF-α polypeptides that compete with the EGF receptor are disclosed in U.S. Pat. No. 4,816,561 issued Mar. 28, 1989.

A putatively hydrophilic region of reurine retroviral envelope protein p15E has been identified that inhibits stimulated T-lymphodyto proliferation. Schmidt et al., *Proc. Natl. Acad. Sci. U.S.A.*, 84:7290–7294 (1987). U.S. Pat. No. 4,822,606 issued Apr. 18, 1989 to R. Snyderman et al. discloses a class of immunosuppressive peptides that are based on a 26-amino acid is sequence, or part thereof, that is conserved among a variety of retroviruses associated with immunosuppression, including reurine and feline leukemia virus, human retrovirus, and a semian virus that causes AIDS in monkeys. One of these peptides (designated CKS-17) was synthesized to correspond to the conserved region of p15E and tested for its effect on a variety of immune cell functions. In addition, peptides corresponding to the conserved regions of the human retroviruses HTLV-I, -II, and -III were synthesized and similarly tested. These peptides have the formula: A-Gln-B-Arg-C-D-E-F-G-H-I-J-K-L-M-N-0, wherein:

A is Leu, Ala, or Tyr;
B is Asn or Ala;
C is Arg, Leu, or Ile;
D is Gly, Ala, or Leu;
E is Leu or Ala;
F is Asp or Val;
G is Leu, Tyr, Glu, or Ile;
H is Leu or Arg;
I is Phe, Leu, Tyr, or Thr;
J is Leu, Trp, or Ala;
K is Lys, Glu, Gln, or Ala;
L is Clu, Gln, or Asp;
M is Gly or Gln;
N is Gly or Gln; and
O is Leu, Val, or Ile.

Immune modulators have applications in various fields involving the immune system. For example, they are useful in preventing graft rejection, preventing autoimmunity, or alleviating inflammatory reactions mediated by immune disorders. Immune modulators typically have suffered from numerous undesirable and substantial side effects.

Accordingly, it is an object of the present invention to provide immune modulators having transforming growth factor-beta-like activity without suffering from undesirable side effects.

It is another object to provide a novel class of immune modulators that are useful as immunogens to elicit antibodies to TGF-β, i.e., TGF-β antagonists.

It is another object to provide a novel class of immune modulators that are useful to develop diagnostic assays for the presence in patient fluids of immunosuppressive proteins such as TGF-β, or antibodies to such proteins.

These and other objects will become apparent to those skilled in the art.

SUMMARY OF THE INVENTION

The above objects are achieved by the provision of a polypeptide comprising an amino acid sequence of the formula:

A-Arg-B-C-D-E-F-G-H-I-J-K, wherein:

A is Val, Leu, Ala, or Tyr or a polypeptide that has at its C-terminus any one of the amino acids Val, Leu, Ala, or Tyr, and that, if greater than 15 residues, does not have the sequence of mature or precursor TGF-β at a homologous location in the mature or precursor TGF-β molecule;
B is Leu, Asn, Ala, Pro, Arg, or Gln;
C is Arg or Leu;
D is Arg, Leu, Ile, or Tyr;
E is Gly, Ala, Leu, Ile;
F is Asp, Leu, or Ala;
G is Asp, Val, or Phe;
H is Arg, Lys, Leu, Tyr, Glu, or Ile;
I is Lys, Arg, Gln, or Leu;
J is Asp, Leu, Phe, Tyr, or Thr; and
K is Leu, Trp, or Ala, or a polypeptide that has at its N-terminus any one of the amino acids Leu, Trp, or Ala, and that, if greater than 15 residues, does not have the sequence of mature or precursor TGF-β at a homologous location in the mature or precursor TGF-β molecule; and physiologically acceptable salts or esters thereof; provided, however, that the polypeptide excludes (a) a full-length mature TGF-β molecule or precursor TGF-β molecule or deletion variants of mature or precursor TGF-β molecules in which from about 1 to 10 amino acid residues have been deleted, (b) a polypeptide of the sequence: Cys-Val-Arg-Gln-Leu-Tyr-Ile-Asp-Phe-Arg-Lys-Asp-Leu-Gly-Trp-Lys, and (c) a polypeptide of the sequence: Arg-Asn-Leu-Glu-Glu-Asn-Cya-Cys-Val-Arg-Pro-Leu-Tyr-Ile-Asp-Phe-Arg-Gln-Asp-Leu.

In another embodiment, the invention provides a polypeptide that excludes (a)–(c) above, said polypeptide comprising an amino acid sequence of the formula:

X-A-Arg-B-C-D-E-F-G-H-I-J-K, wherein:

X is Cys or a crosslinker moiety or a polypeptide that has at its C-terminus a Cys, and that, if greater than 15 residues, does not have the sequence of mature or precursor TGF-β at a homologous location in the mature or precursor TGF-β molecule; A is Val, Leu, Ala, or Tyr; and B-K are defined above.

In another embodiment, the invention herein provides a polypeptide as described above wherein K is a polypeptide having its N-terminal amino acid followed by the sequence L-M-N, wherein:

L is Gly, Leu, Glu, Gln, or Ala;
M is Trp, Glu, Gln, or Asp; and
N is Lys, Gly, or Gln.

In a preferred embodiment, the polypeptide is coupled to a carrier protein such as bovine serum albumin or human serum albumin, a sugar group, or a lipid.

Also provided herein is a polypeptide polymer comprising at least two polypeptide chains crosslinked to each other, each comprising the amino acid sequence identified above.

In another embodiment, the invention provides a method of ameliorating an immune or inflammatory disorder in an animal comprising administering to that animal a therapeutically effective amount of the polypeptide polymer identified above that has the sequence containing the X moiety at the N terminus.

In yet another embodiment, the invention furnishes a suppository for the treatment of inflammatory bowel disease that contains a therapeutically effective amount of the polypeptide polymer identified above that has the sequence containing the X moiety at the N terminus.

In a still further embodiment, the invention provides a composition comprising the polypeptide polymer identified above having the sequence containing the X moiety at the N terminus and a substance selected from the group consisting of an antagonist to γ-interferon, an antagonist to TGF-α, an antagonist to TNF-α, an antagonist to TNF-β an antagonist to IL-1α or β, a nonsteroidal anti-inflammatory agent, penicillamine, salicylate, and a gold salt.

In a still further embodiment, the invention comprises a method for producing antibodies that neutralize immunosuppressive proteins comprising immunizing an animal with the polypeptide identified above that has the sequence containing the X moiety and isolating antibodies generated by the polypeptide that neutralize at least one immunosuppressive protein, preferably TGF-β.

In yet another embodiment, the invention provides a monoclonal antibody specific for the polypeptide identified above and its various labeled and immobilized forms.

In another embodiment, the invention provides a method for blocking immunosuppressive activity of an animal caused by an immunosuppressive protein comprising identifying the responsible immunosuppressive protein and contacting the protein with a monoclonal antibody generated from the polypeptide that neutralizes the protein. If the antibody is immobilized, the protein will be immobilized when it is bound to the antibody.

In another aspect, the invention supplies a method for detecting the presence of an immunosuppressive protein in a sample comprising contacting the sample with a labeled version of the monoclonal antibody generated from the polypeptide herein. The sample can also be contacted with an immobilized antibody that binds to a different epitope of the immunosuppressive protein than the one to which the labeled antibody binds.

In a still further aspect, the invention furnishes a method for accelerating the healing of a wound in an animal comprising applying to the wound a wound-accelerating effective amount of the polypeptide polymer described above.

In a still further aspect, the invention provides a process for obtaining a therapeutically biologically active polypeptide polymer comprising the steps of assaying a monomeric polypeptide and determining that it is not therapeutically biologically active, and crosslinking the monomeric polypeptide at one of its termini with at least one polypeptide chain homologous to the monomeric polypeptide, so as to form a polymer of the monomeric polypeptide. Preferably the monomeric polypeptide is the TGF-β peptide described herein.

A novel class of polypeptides and analogs thereof have been discovered that are based on a 16 amino acid sequence, or part thereof, which is strikingly well conserved among a variety of proteins in the TGF-β family. These proteins include TGF-β1, TGF-β2, TGF-β3, the inhibin alpha and beta chains, decapentaplegic protein (dpp), and the bone morphogenic proteins known as BMP2, BMP3, and BMP4, the latter class of proteins being described by Wozney at al., Science, 24:1528–1534 (1988).

DESCRIPTION OF THE PREFERRED EMBODIMENTS

A. Definitions

Figure 1:
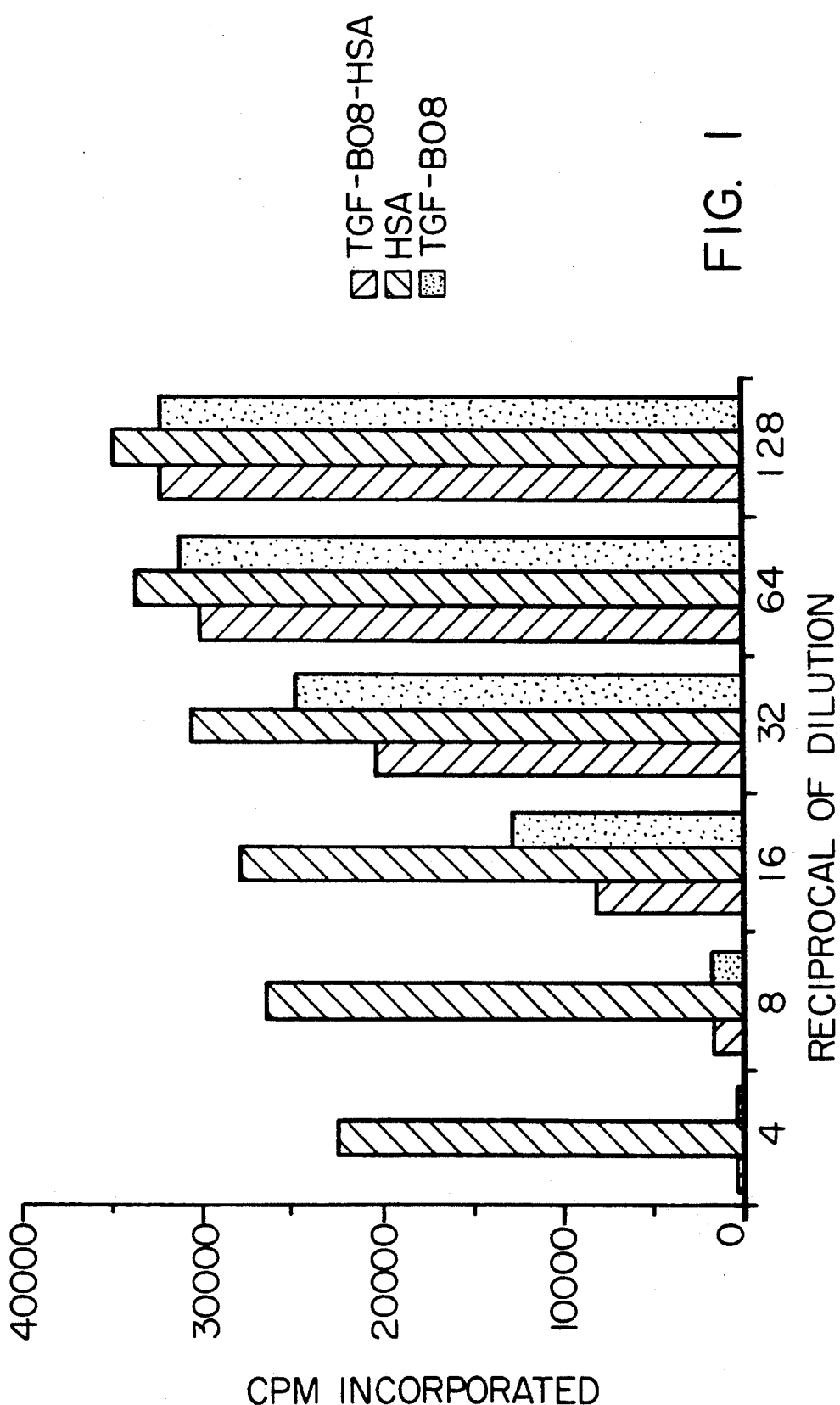
FIG. 1 represents a bar graph of the amount of cpm incorporated in the CCL-64 mink lung cell proliferation assay versus the reciprocal of dilution of a TGF-β polypeptide conjugated to HSA (black), HSA control (hatched), and the unconjugated polypeptide (checked).

As used herein, the terms "mature TGF-β," "TGF-β," and "precursor TGF-β" refer to the family of molecules described hereinabove that have either the full-length, native amino acid sequence of any of the TGF-βs from any species but lacking the signal sequence ("mature") or the full-length, native amino acid sequence of any of the TGF-βs from any species with the naturally occurring signal sequence, including the latent forms and associated or unassociated complex of precursor and mature TGF-β ("precursor"). Reference to such full-length TGF-β herein will be understood to be a reference to any one of the currently identified forms, including TGF-β1, TGF-β2 and TGF-β3.

The sequence "Cys-Val-Arg-Gln-Leu-Tyr-Ile-Asp-Phe-Arg-Lys-Asp-Leu-Cly-Trp-Lys" is the 16-mer that is the subject of copending U.S. application Ser. No. 07/356,965 filed May 25, 1989, now abandoned, supra. The sequence "Arg-Asn-Leu-Glu-Glu-Asn-Cys-Cys-Val-Arg-Pro-Leu-Tyr-Ile-Asp-Phe-Arg-Gln-Asp-Leu" is the 20-mer derived from TGF-β3 that is described in EP 267,463, supra.

As used herein, the term "carrier protein" refers to a protein that is conjugated to the polypeptide either to increase its molecular weight for purposes of increasing activity or immunogenicity of the polypeptide, to confer stability to the molecule, to increase its biological activity, or to increase its serum half-life. Such carrier proteins include, for example, keyhole limpet hemocyanin, serum proteins such as transferrin, bovine serum albumin, or human serum albumin, immunoglobulins, or hormones, such as insulin. Preferably the carrier protein is bovine serum albumin, human serum albumin, an immunoglobulin, or a hormone, and most preferably is human serum albumin. A "sugar group" and a "lipid" refer, respectively, to any sugar moieties such as mannose or dextrose groups, and to lipids, including phospholipids.

As used herein, the term "protein to be rendered non-immunogenic or tolerogenic" refers to a protein that is desired to be made non-immunogenic or inert to reactions with existing antibodies. Typically, such proteins are xenogeneic to the peptide and must be administered over a long period of time, such as anti-thymocyte globulin or reurine monoclonal antibodies to tumor-specific antigens, as well as anti-Fe receptor antibodies, anti-toxin antibodies (e.g., antibodies to tetanus toxin), and anti-idiotype antibodies.

As used herein, the term "immune disorder" refers to an immune-mediated disease such as a cell-mediated immune reaction, generally characterized by tissue destruction and/or the influx of inflammatory cells. Examples of immune disorders include, e.g., organ allograft rejection and autoimmune diseases, such as systemic lupus erythematosus, rheumatoid arthritis, scleroderma, dermatomyositis, polymyositis, unclassified connective diseases, autoimmune hemolytic anemia, idiopathic thrombocytopenic purpura, autoimmune thyroiditis, polyarteritis nodosum, glomerulonephritis, uveitis, etc.

As used herein, the term "immunosuppressive protein" as used in the context that it is neutralized by antibodies generated by the polypeptide herein generally refers to the protein to which the polypeptide corresponds that exhibits immunosuppressive activity. For example, a polypeptide representing an internal, active sequence within the full-length TGF-$\beta$ sequence would have TGF-$\beta$ as its immunosuppressive protein to be neutralized.

As used herein, the term "inflammatory disorder" refers to an inflammation-mediated malady, whether or not also immune mediated. Thus, such diseases include those caused by the release of toxic oxygen products from phagocytes in inflammatory lesions. Examples include rheumatoid arthritis, adult respiratory distress syndrome, and septic shock.

Inflammatory responses associated with various immune disorders are typically divided into four classes. Class I responses are reaginic or allergic reactions characterized by atrophy or anaphylaxis. Class II responses are dependent upon cytotoxic antibody and are associated, for example, with autoimmune hemolytic anemia and thrombocytopenia attendant to systemic lupus erythemahosus (SLE). Class III responses are characterized by chronic generation of immune complexes containing IgG and/or IgM. Class IV responses, associated with delayed hypersensitivity, are mediated by cytokines and T-lymphocytes and are typically found in tuberculosis, sarcoidosis, polymyositia, granulomatosis, and vasculitis. This invention is particularly concerned with inappropriate or aberrant class II and class III responses. These classes are generally associated with inflammatory sequelae dependent upon chronic immune dysfunction, including constitutive production of soluble mediators such as cytokines, immunoglobulins, and complement components.

As used herein, "animal" refers to species that are capable of suffering from immune or inflammatory disorders, preferably mammals, and most preferably humans.

As used herein, "label moiety" refers to labels that may be detected directly, such as fluorochromes or radiolabels, as well as moieties, such as enzymes, that must be reacted or derivatized to be detected. Examples of such label moieties are $^{32}P$, $^{125}I$, $^{3}H$, $^{14}C$, fluorescein and its derivatives, rhodamine and its derivatives, dansyl, umbelliferone, luciferin, 2,3-dihydrophthalazinediones, horseradish paroxidase, alkaline phosphatase, beta-galactosidase, lysozyme, and glucose-6-phosphate dehydrogenase.

As used herein, the term "epitope" refers to a specific site on the immunosuppressive protein to which only certain antibodies bind. Thus, the term refers to a specific antigenic determinant on the immunosuppressive protein.

As used herein, the term "sample," used in the context of immunometric assays, refers to any liquid or biological sample that contains or may contain the immunosuppressive protein to be detected. The sample includes fluids such as human or animal body fluids, e.g., blood, serum, urine, amniotic fluid, tissue extracts, cerebrospinal fluid, and the like. The samples may require special treatment such as extraction before being analyzed, depending on the tendency of the relevant antigens contained therein toward lability, aggregation, or absorption by the storage container.

As used herein, the term "polypeptide" refers to a peptide having at least two, and preferably more than two amino acids. "Monomeric polypeptide" refers to a polypeptide that is a monomer as opposed to a dimer or polymer in the sense that it is not crosslinked or otherwise bonded to another homologous polypeptide chain. The term "polymer" refers to a moiety wherein at least two monomeric polypeptides are crosslinked to each other, and "dimer" refers to a moiety wherein two monomeric polypeptides are crosslinked to each other.

As used herein, the term "homologous," when used in the context of the formation of a polymer, refers to a polypeptide chain with an amino acid sequence that is at least 80% homologous with the sequence of a monomeric polypeptide chain to be polymerized.

The word "crosslinking" as used herein refers both to the linking of one polypeptide chain to the amino acid side groups of another polypeptide chain and to the linking of one polypeptide moiety through the terminal carboxyl or amino groups of a second polypeptide chain.

The expression "crosslinking moiety" refers to a linking moiety conferred by an external crosslinking agent used to crosslink the polypeptide with one or more polypeptides as described further hereinbelow.

The expression "pharmacologically acceptable salts and esters thereof" refers to inorganic or organic salts such as metal salts and acid addition salts thereof and lower (e.g., $C_{1-4}$) alkyl esters of the polypeptides. Examples include salts of alkaline earths (e.g., sodium or magnesium), ammonium or $NX_4^+$ (wherein X is $C_{1-4}$ alkyl), organic carboxylic acids such as acetic, lactic, tartaric, malic, isethionic, lactobionic, and succinic acids; organic sulfonic acids such as methanesulfonic, ethanesulfonic, benzenesulfonic, and p-toluenesulfonic acids; and inorganic acids such as hydrochloric, sulfuric, phosphoric, and sulfamic acids. Salts of a polypeptide with a hydroxy group include the anion of said polypeptide in combination with a suitable cation such as Na+, NH4+, and NX4+ (wherein X is a C1-4 alkyl group).

"Biologically active" polypeptides herein are defined as those having the ability to cross-react with antisera raised against native TGF-β (where native TGF-β is that which is obtained from platelets or other natural sources). Immunological crossreactivity is a measure of a single active epitope and does not necessarily encompass an active domain involved in immunosuppressive activity.

"Therapeutic biological activity" and "therapeutically biologically active" refer to activity that not only encompasses biological activity as defined above, but also the ability to inhibit the proliferation of a cultured established mink lung cell line CCL 64 and/or to inhibit the proliferation of human lymphocytes to an antigen such as tetanus toxoid and/or to mitogens such as phytohemagglutinin P (PHA-P) or Concanavalin A (ConA). Polypeptides with therapeutic biological activity are preferred.

B. Modes for Carrying Out the Invention

The polypeptide herein comprises at least the 12-mer described above and additionally exhibits biological activity. It is noted that the flanking residues of the 12-mer specified are amino acids or polypeptides. If these residues are polypeptides, they have the specified amino acid at their N- or C-terminus. In addition, if they consist of more than 15 residues, and more preferably more than 10 residues, and most preferably more than 5 residues, including the residue specified at their N- or C-terminus, they do not have the sequence of mature or precursor TGF-β at an analogous (homologous) position in the corresponding native mature or precursor TGF-β molecule. This language thus excludes polypeptide fragments of native TGF-β that may have been obtained incidentally by random digestion of the native molecule with a cleaving agent such as trypsin.

Preferably, the polypeptide comprises the 13-mer specified above containing the X moiety, wherein most preferably the X is a cysteine residue, and more preferably the polypeptide is the 16-mer described above ending in the sequence L-M-N, as described above. More preferably, the 16-mer is derived from a TGF-β, and comprises the sequence:

Cys-A-Arg-B-Leu-Tyr-Ile-Asp-Phe-H-I-Asp-Leu-Gly-Trp-Lys, wherein
A is Val or Leu;
B is Pro or Gln;
H is Arg or Lys; and
I is Lys, Arg, or Gln.

More preferably, the 16-mer comprises the sequence:

Cys-Val-Arg-B-Leu-Tyr-Ile-Asp-Phe-Arg-I-Asp-Leu-Gly-Trp-Lys wherein:
B is Pro or Gln; and
I is Lys or Gln.

In the latter formula, preferably if B is Gln, I is Lys and if B is Pro, I is Gln.

Alternatively, the 16-mer is selected to comprise the amino acid sequence:

Cys-Leu-Arg-Pro-Leu-Tyr-Ile-Asp-Phe-Lys-Arg-Asp-Leu-Gly-Trp-Lys.

The polypeptide is suitably used alone, presumably because it polymerizes in situ when exposed to air or added oxygen, but is preferably coupled to another material or crosslinked to itself to increase its biological or immunological activity, particularly if the polypeptide is relatively short, or to bestow certain properties on the material being coupled. For example, the polypeptide is suitably coupled to a carrier protein, sugar group, or lipid, the type of which will depend on the particular utility and size of the polypeptide.

Alternatively, the polypeptides can be coupled to proteins that one wishes to render non-immunogenic or tolerogenic, or they can be crosslinked. Coupling can be accomplished using methods well known to those skilled in the art, such as, e.g., that described in Cianciolo et al., Science, 453 (1985).

In fact, in a specific aspect of this invention, any appropriate polypeptide, provided that it is determined to be inactive, may be polymerized to increase its activity and to facilitate its delivery in vivo. This process involves the steps of assaying a monomeric polypeptide and determining if it is biologically active (generally using bioassays that determine its immunologic or therapeutic utility). Thus, for example, an indication of biological activity is whether the monomeric peptide neutralizes monoclonal and polyclonal antibodies raised against a corresponding native protein known to have biological/therapeutic activity, e.g., mature-human TGF-β. Other indications, specific for the TGF-β polypeptide herein, include whether the peptide stimulates release of PGE2 by IL-1 treated human fibroblasts, interferes with the binding of full-length TGF-β to its receptors, or acts as an immunosuppressive agent either in vitro or in vivo in an animal model. The first step, then, involves determining that the monomeric polypeptide is inactive in one or more of these assays.

If the polypeptide is inactive, then it is placed into a polymerized form and is at least dimerized. This is accomplished by introducing a moiety between two or more substantially homologous replicates of the inactive polypeptide that links the monomer chains in such a fashion as to achieve or restore the desired biological activity. In general, a chain is crosslinked at one of its termini with a second polypeptide chain that is at least 80% homologous to the sequence of the monomeric polypeptide, preferably at least 90%, and most preferably 100%, so as to form a biologically active polymer, preferably a dimer. The polymer may be formed in situ by allowing the monomer to oxidize (e.g., for disulfide bonds) or it may be synthesized by using a specific crosslinking agent. In either case, the polymer is preferably recovered in the last step of this process.

The crosslinking between the polypeptide chains is at either end of the polypeptide, depending on which end is most appropriate. For example, if the N-terminus of the polypeptide comprises a cysteinyl residue, this end is preferably crosslinked by linking it to a second cysteinyl residue on the homologous polypeptide chain, thereby forming a cystinyl bond.

Polypeptide chains are polymerized by crosslinking monomer chains with polyfunctional crosslinking agents, either directly or indirectly through multifunctional polymers. Ordinarily, two substantially identical polypeptides are crosslinked at their C or N termini using a bifunctional crosslinking agent. The agent is used to crosslink the terminal amino and/or carboxyl groups. Generally, both terminal carboxyl groups or both terminal amino groups are crosslinked to one another, although by selection of the appropriate crosslinking agent the alpha amino group of one polypeptide is crosslinked to the terminal carboxyl group of the other polypeptide. Preferably, the polypeptides are substituted at their C-termini with cysteine. Under conditions well known in the art a disulfide bond can be formed between the terminal cysteines, thereby crosslinking the polypeptide chains. Selection of the crosslinking agent will depend upon the identities of the reactive side chains of the amino acids present in the polypeptides. For example, disulfide crosslinking would not be preferred if cysteine was present in the polypeptide at additional sites than the C-terminus.

Suitable crosslinking sites on the peptides, aside from the N-terminal amino and C-terminal carboxyl groups, include epsilon amino groups found on lysine residues, as well as amino, imino, carboxyl, sulfhydryl and hydroxyl groups located on the side chains of internal residues of the peptides or residues introduced into flanking sequences A, X, and K. Crosslinking through externally added crosslinking agents is suitably achieved, e.g., using any of a number of reagents familiar to those skilled in the art, for example, via carbodiimide treatment of the polypeptide. Other examples of suitable multifunctional (ordinarily bifunctional) crosslinking agents include 1,1-bis(diazoacetyl)-2-phenylethane; glutaraldehyde; N-hydroxysuccinimide esters (Bragg and Hou, *Arch. Biochem. Biophys.* 167:311–321 [1975]; Anjaneyla and Staros, *Int. J. Pep. Pro. Res.* 30:117–124 [1987]), such as esters with 4-azidosalicylic acid; homobifunctional imidoesters including disuccinimidyl esters such as 3,3'-dithiobis (succinimidyl-propionate) and dimethyl adipimidate dihydrochloride (Zahn, *Agnew. Chem.*, 67:561–572 [1955]; Golden and Harrison, *Biochemistry* 21: 3862–3866 (19821); bifunctional maleimides such as bis-N-maleimido1,8-octane; disuccinimidyl suberate (Novick et al., *J. Biol. Chem.* 262:8483–8487 [1987]), bis(sulfosuccinimidyl) suberate (Lee and Conrad, *J. Immunol.* 134:518–525 [1985]); heterobifunctional crosslinking reagents (Loments and Fairbanks, *Arch. Biochem. Biophys.* 167:311–321 [1976]; Anjaneyula and Staros, supra; Partis et al., *J. Pro. Chem.* 2:263–277 [1983]; Weltman et al., *BioTechniques,* 1:148–152 [1983]; Yoshtake et al., *J. Biochem.* 92:1423–1424 [1982])), including those with an N-hydroxysuccinimide moiety at one end and a maleimido group on the other end; succinimidyl 4-(N-maleimidomethyl)cyclohexane-1-carboxylate (SMCC) (Mahan et al., *Anal. Biochem.* 162:163–170 (1987]); sulfo-SMCC (Hashida et al., *J. Applied Biochem.* 6:56–63 [1984]); m-maleimidobenzoyl-N-hydroxysuccinimide ester (MBS); sulfo-MBS; suceinimidyl 4-(p-maleimidophenyl)butyrate (SMPB); sulfo-SMPB; N-succinimidyl(4-iodoacetyl)aminobenzoate (SIAB); sulfo-SIAB; 1-ethyl-3-(3-dimethylaminopropyl)carbodiimide hydrochloride (EDC); and N-hydroxysulfosuccinimide. Crosslinking agents such as methyl-3-[(p-azidophenyl)dithio) propioimidate yield photoactivatable intermediates which are capable of forming crosslinks in the presence of light. If necessary, sensitive residues such as the side chains of the diargininyl group are protected during crosslinking and the protecting groups removed thereafter.

Polymers capable of multiple crosslinking serve as indirect crosslinking agents. For example, cyanogen bromide activated carbohydrates and the systems described in U.S. Pat. Nos. 3,959,080; 3,969,287; 3,691,016; 4,195,128; 4,247,642; 4,229,537; 4,055,635 and 4,330,440 are suitably modified for crosslinking the peptides herein. Crosslinking to amino groups of the peptides is accomplished by known chemistries based upon eyanuric chloride, carbonyl diimidazole, aldehyde reactive groups (PEG alkoxide plus diethyl acetal of bromoacetaldehyde; PEG plus DMSO and acetic anhydride, or PEG chloride plus the phenoxide of 4-hydroxybenzaldehyde). Also useful are succinimidyl active esters, activated dithiocarbonate PEG, and 2,4,5-trichlorophenylchloroformate- or p-nitrophenylchloroformate-activated PEG. Carboxyl groups are derivatized by coupling PEG-amine using carbodiimide. Ordinarily, however, the crosslinking agent is not a multifunctional polymer but instead is a small molecule being less than about 500 in MW.

Also within the scope of this invention are cyclized polypeptides, including those containing about from 1 to 3 repeating polypeptide units, in which the amino terminus of a polypeptide is bonded to its carboxy terminus or "head to tail" to the carboxy terminus of another substantially identical polypeptide chain. Substantially identical polypeptides are those that exhibit the same qualitative immunosuppressive activity, notwithstanding the degree of amino acid sequence homology among the polypeptides. Sequence homology within the confines provided herein is immaterial. What is relevant is that the polypeptides act as immunosuppressive agents. Those variants that are capable of doing so are used as subunits in homo or heteropolymers.

The attachment of a sugar group or lipid can be directly to the polypeptide in a manner well known to those skilled in the art, with the only requirement being that the polypeptide structure not be affected so as to result in the loss of its biological activity. It is understood that when mention is made below of use of polypeptides, the coupled and crosslinked molecules are also intended to be included.

The nomenclature used to define the peptides is that specified by Schroder & Lubke, "The Peptides," Academic Press (1965), wherein in accordance with conventional representation the amino group at the N-terminus appears to the left and the carboxyl group at the C-terminus to the right. Included within the scope of this invention are the D and L stereoisomers of such amino acids when the structure of the amino acid admits of stereoisomeric forms. For the purposes of this application, a named amino acid shall be construed to include both the D or L stereoisomers, preferably the L stereoisomer, if the amino acid can exist in stereoisomeric form.

For the purposes of this application, proline shall be construed to include hydroxylproline, loucine to include norleutine, lysine to include hydroxylysine, serene to include 3-phosphoserine, homoserine and 0-phosphohomoserine, tyrosine to include dihydroxyphenylalanine, tryptophan to include 5-hydroxytryptophan, cysteine to include S-methylcysteine and thiocysteine, histidine to include 1-methylhistidine and 3-methylhistidine, alanine to include $\beta$-alanine, and aspartic acid to is include $\beta$-aspartyl phosphate.

The peptides are synthesized by any suitable method, such as, for example, by exclusively solid-phase techniques, by partial solid-phase techniques, by fragment condensation, by classical solution couplings, by recombinant DNA techniques, i.e., by fermentation of a genetically engineered host cell transformed with an expression vector containing a gene coding for the relevant polypeptide, and by a combination of both genetic engineering methods and peptide synthesis.

Techniques for exclusively solid-phase synthesis are set forth in "Solid-Phase Peptide Synthesis," Steward & Young, (Freeman & Co., San Francisco, 1969) and U.S. Pat. No. 4,105,603, issued Aug. 8, 1978. Classical solution synthesis is described in detail in the treatise "Methoden der Organischen Chemie (Houben-Weyl): Synthese von Peptiden," E. Wunsch (ed.) (1974), Georg Thieme Verlag, Stuttgard, W. Ger. The fragment condensation method of synthesis is exemplified in U.S. Pat. No. 3,972,859 issued Aug. 3, 1976. Other available syntheses are exemplified by U.S. Pat. No. 3,842,067 issued Oct. 15, 1974 and U.S. Pat. No. 3,862,925 issued Jan. 28, 1975.

When peptides are not prepared using recombinant DNA technology, they are preferably prepared using solid-phase synthesis, such as that generally described by Merrifield, *J. Am. Chem. Soc.*, 85:2149 (1963), although other equivalent chemical syntheses known in the art are employable as previously mentioned. Solid-phase synthesis is initiated from the C-terminus of the peptide by coupling a protected α-amino acid to a suitable resin. Such a starting material can be prepared by attaching an α-amino-protected amino acid by an ester linkage to a chloromethylated resin or a hydroxymethyl resin, or by an amide bond to a BHA resin or MBHA resin. The preparation of the hydroxymethyl resin is described by Bodansky et al., *Chem. Ind.* (London) 38:1597-1598 (1966). Chloromethylated resins are commercially available from BioRad laboratories, Richmond, Calif. and from Lab. Systems, Inc. The preparation of such a resin is described by Stewart et al., "Solid Phase Peptide Synthesis" (Freeman & Co., San Francisco 1969), Chapter 1, pp. 1–6. BHA and MBHA resin supports are commercially available and are generally used only when the desired polypeptide being synthesized has an unsubstituted amide at the C-terminus.

The amino acids are coupled to the peptide chain using techniques well known in the art for the formation of peptide bonds. One method involves converting the amino acid to a derivative that will render the carboxyl group more susceptible to reaction with the free N-terminal amino group of the peptide fragment. For example, the amino acid can be converted to a mixed anhydride by reaction of a protected amino acid with ethyl chloroformate, phenyl chloroformate, sec-butyl chloroformate, isobutyl chloroformate, pivaloyl chloride, or like acid chlorides. Alternatively, the amino acid can be converted to an active ester such as a 2,4,5-trichlorophenyl ester, a pentachlorophenyl ester, a p-nitrophenyl ester, a N-hydroxysuccinimide ester, or an ester formed from 1-hydroxybenzotriazole.

Another coupling method involves use of a suitable coupling agent such as N,N'-dicyclohexylcarbodiimide or N,N'-diisopropylcarbodiimide. Other appropriate coupling agents, apparent to those skilled in the art, are disclosed in E. Gross & J. Meienhofer, *The Peptides: Analysis, Structure, Biology*, Vol. 1: Major Methods of Peptide Bond Formation (Academic Press, New York, 1979).

It should be recognized that the α-amino group of each amino acid employed in the peptide synthesis must be protected during the coupling reaction to prevent side reactions involving the reactive α-amino function. It should also be recognized that certain amino acids contain reactive side-chain functional groups (e.g., sulfhydryl, amino, carboxyl, and hydroxyl), and that such functional groups must also be protected with suitable protecting groups to prevent a chemical reaction from occurring at that site during both the initial and subsequent coupling steps. Suitable protecting groups, known in the art, are described in E. Gross & J. Meienhofer, *The Peptides: Analysis, Structure, Biology*, Vol. 3: Protection of Functional Groups in Peptide Synthesis (Academic Press, New York, 1981).

In the selection of a particular side-chain protecting group to be used in synthesizing the peptides, the following general rules are followed. An α-amino protecting group (a) must render the α-amino function inert under the conditions employed in the coupling reaction, (b) must be readily removable after the coupling reaction under conditions that will not remove side chain protecting groups and will not alter the structure of the peptide fragment, and (c) must eliminate the possibility of racemization upon activation immediately prior to coupling. A side-chain protecting group (a) must render the side chain functional group inert under the conditions employed in the coupling reaction, (b) must be stable under the conditions employed in removing the α-amino protecting group, and (c) must be readily removable upon completion of the desired amino acid peptide under reaction conditions that will not alter the structure of the peptide chain.

It will be apparent to those skilled in the art that the protecting groups known to be useful for peptide synthesis will vary in reactivity with the agents employed for their removal. For example, certain protecting groups such as triphenylmethyl and 2-(p-biphenylyl)isopropyloxycarbonyl are very labile and can be cleaved under mild acid conditions. Other protecting groups, such as t-butyloxycarbonyl (BOC), t-amyloxycarbonyl, adamantyloxycarbonyl, and p-methoxybenzyloxycarbonyl, are less labile and require moderately strong acids, such as trifluoroacetic acid hydrochloric acid or boron trifluoride in acetic acid, for their removal. Still other protecting groups, such as benzyloxycarbonyl (CBZ or Z), halobenzyloxycarbonyl, p-nitrobenzyloxycarbonyl, cycloalkyloxycarbonyl, and isopropyloxycarbonyl, are even less labile and require stronger acids, such as hydrogen fluoride, hydrogen bromide, or boron trifluoroacetate in trifluoroacetic acid, for their removal.

Among the classes of useful amino acid protecting groups are included:

(1) for an α-amino group, (a) aromatic urethane-type protecting groups, such as fluorenylmethyloxycarbonyl (FMOC), CBZ, and substituted CBZ, such as, e.g., p-chlorobenzyloxycarbonyl, p-nitrobenzyloxycarbonyl, p-bromobenzyloxycarbonyl, and p-methoxybenzyloxycarbonyl, o-chlorobenzyloxycarbonyl, 2,4-dichlorobenzyloxycarbonyl, 2,6-dichlorobenzyloxycarbonyl, and the like; (b) aliphatic urethane-type protecting groups, such as BOC, t-amyloxycarbonyl, isopropyloxycarbonyl, 2-(p-biphenylyl)isopropyloxycarbonyl, allyloxycarbonyl, and the like; and (c) cycloalkyl urethane-type protecting groups, such as cyclopentyloxycarbonyl, adamantyloxycarbonyl, and cyclohexyloxycarbonyl. The preferred α-amino protecting group is BOC.

(2) for the side chain amino group present in Lys, protection may be by any of the groups mentioned above in (1) such as BOC, p-chlorobenzyloxycarbonyl, etc.

(3) for the guanidine group of Arg, protection may be by nitro, tosyl, CBZ, adamantyloxycarbonyl, and BOC.

(4) for the hydroxyl group of Ser, Thr, or Tyr, protection may be, for example, by $C_1$–$C_4$ alkyl, such as methyl, ethyl, and t-butyl; benzyl (BZL); substituted BZL, such as p-methoxybenzyl, p-nitrobenzyl, p-chlorobenzyl, o-chlorobenzyl, and 2,6-dichlorobenzyl.

(5) for the carboxyl group of Asp or Glu, protection may be, for example, by esterification using groups such as BZL, t-butyl, cyclohexyl, cyclopentyl, and the like.

(6) for the imidazole nitrogen of His, the tosyl moiety is suitably employed.

(7) for the phenolic hydroxyl group of Tyr, a protecting group such as tetrahydropyranyl, tert-butyl, trityl, BZL, chlorobenzyl, 4-bromobenzyl, and 2,6-dichlorobenzyl are suitably employed. The preferred protecting group is 2,6-dichlorobenzyl.

(8) for the side chain amido group of Asn or Gln, xanthyl (Xan) is preferably employed.

(9) for Met, the amino acid is preferably left unprotected.

(10) for the thio group of Cys, p-methoxybenzyl is typically employed.

The C-terminal amino acid, e.g., Lys, is protected at the N-amino position by an appropriately selected protecting group, in the case of Lys, BOC. The BOC-Lys-OH can be first coupled to the benzhydrylamine or chloromethylated resin according to the procedure set forth in Horiki et al., *Chemistry Letters*, 165–168 (1978) or using isopropylcarbodiimide at about 25° C. for 2 hours with stirring. Following the coupling of the BOC-protected amino acid to the resin support, the α-amino protecting group is removed, as by using trifluoroacetic acid (TFA) in methylene chloride or TFA alone. The deprotection is carried out at a temperature between about 0° C. and room temperature. Other standard cleaving reagents, such as HCl in dioxane, and conditions for removal of specific α-amino amino protecting groups are described in Schroder & Lubke, supra, Chapter I, pp. 72–75.

After removal of the α-amino protecting group, the remaining α-amino and side-chain protected amino acids are coupled stepwise in the desired order. As an alternative to adding each amino acid separately in the synthesis, some may be coupled to one another prior to addition to the solid-phase synthesizer. The selection of an appropriate coupling reagent is within the skill of the art. Particularly suitable as a coupling reagent is N,N'-dicyclohexyl carbodiimide or diisopropylcarbodiimide.

Each protected amino acid or amino acid sequence is introduced into the solid-phase reactor in excess, and the coupling in suitably carried out in a medium of dimethylformamide (DMF) or $CH_2Cl_2$ or mixtures thereof. If incomplete coupling occurs, the coupling procedure is repeated before removal of the N-amino protecting group prior to the coupling of the next amino acid. The success of the coupling reaction at each stage of the synthesis may be monitored. A preferred method of monitoring the synthesis is by the ninhydrin reaction, as described by Kaiser et al., *Anal. Biochem.*, 34:595 (1970). The coupling reactions can be performed automatically using well known methods, for example, a Biosearch 9500 Peptide Synthesizer.

Upon completion of the desired peptide sequence, the protected peptide must be cleaved from the resin support, and all protecting groups must be removed. The cleavage reaction and removal of the protecting groups is suitably accomplished simultaneously or stepwise. When the resin support is a chloromethylated polystyrene resin, the bond anchoring the peptide to the resin is an ester linkage formed between the free carboxyl group of the C-terminal residue and one of the many chloromethyl groups present on the resin matrix. It will be appreciated that the anchoring bond can be cleaved by reagents that are known to be capable of breaking an ester linkage and of penetrating the resin matrix. One especially convenient method is by treatment with liquid anhydrous hydrogen fluoride. This reagent not only will cleave the peptide from the resin but also will remove all protecting groups. Hence, use of this reagent will directly afford the fully deprotected peptide. When the chloromethylated resin is used hydrogen fluoride treatment results in the formation of the free peptide acids. When the benzhydrylamine resin is used, hydrogen fluoride treatment results directly in the free peptide amines. Reaction with hydrogen fluoride in the presence of anisole and dimethylsulfide at 0° C. for one hour will simultaneously remove the side-chain protecting groups and release the peptide from the resin.

When it is desired to cleave the peptide without removing protecting groups, the protected peptide-resin can undergo methanolysis to yield the protected peptide in which the C-terminal carboxyl group is methylated. The methyl ester is then hydrolyzed under mild alkaline conditions to give the free C-terminal carboxyl group. The protecting groups on the peptide chain then are removed by treatment with a strong acid, such as liquid hydrogen fluoride. A particularly useful technique for methanolysis is that of Moore et al., *Peptides, Proc. Fifth Amer. Pept. Symp.*, M. Goodman and J. Meienhofer, Eds., (John Wiley, N.Y., 1977), p. 518–521, in which the protected peptide-resin is treated with methanol and potassium cyanide in the presence of crown ether.

Another method for cleaving the protected peptide from the resin when the chloromethylated resin is employed is by ammonolysis or by treatment with hydrazins. If desired, the resulting C-terminal amide or hydrazide can be hydrolyzed to the free C-terminal carboxyl moiety, and the protecting groups can be removed conventionally.

It will also be recognized that the protecting group present on the N-terminal α-amino group may be removed preferentially either before or after the protected peptide is cleaved from the resin support.

Purification of the polypeptides of the invention is typically achieved using conventional procedures such as preparative HPLC or other known chromatographic techniques such as gel permeation, ion exchange, partition chromatography, or countercurrent distribution.

The polymeric polypeptides herein have a number of therapeutic uses, including as agents for the prevention of graft rejection, prevention or reduction of autoimmunity, and/or alleviation of inflammatory reactions, as wound acceleration agents, as immunogens to elicit antibodies that block naturally occurring immunosuppressive proteins associated with immunosuppressive activity such as neoplastic or viral diseases and that detect the presence of immune or inflammatory disorders when the early appearance of peptide-related immunosuppressive proteins or of antibodies to such proteins is monitored.

The diseases or disorders to be treated with the polypeptide polymers in accordance with this invention include organ allograft rejection and autoimmune diseases. Preferably, such diseases are those that fall within Classes II and III as described above, in particular inflammatory bowel disease, systemic lupus erythematosus (SLE), and rheumatoid arthritis (RA). These disorders are characterized by severe inflammation accompanied by unusually elevated collagenase production and tissue destruction, and are generally thought to have their origin in an aberrant immune response of an unresolved and poorly understood nature.

For the immune and inflammatory disease indications, the polymeric polypeptides will be formulated and dosed in a fashion consistent with good medical practice taking into account the specific disorder to be treated, the condition of the individual patient, the site of delivery of the polypeptide, the method of administration, and other factors known to practitioners. Thus, for purposes herein, the "therapeutically effective amount" of the polypeptide polymers is an amount that is effective either to prevent, lessen the worsening of, alleviate, or cure the diseased condition.

The polypeptide polymer is prepared for storage or administration by mixing the polypeptide having the desired degree of purity with physiologically acceptable carriers, excipients, or stabilizers. Such materials are non-toxic to recipients at the dosages and concentrations employed. If the conjugate is water soluble, it may be formulated in a buffer such as phosphate or other organic acid salt preferably at a pH of about 7 to 8. If the conjugate is not very soluble in water, it may be prepared as a microemulsion by formulating it with a nonionic surfactant such as Tween, Pluronies, or PEG, e.g., Tween 80, in an amount of 0.04-0.05% (v/v), to increase its solubility.

Optionally other ingredients may be added such as antioxidants, e.g., ascorbic acid; low molecular weight (less than about ten residues) polypeptides, e.g., polyarginine or tripeptides; proteins, such as serum albumin, gelatin, or immunoglobulins; hydrophilic polymers such as polyvinylpyrrolidone; amino acids, such as glycine, glutamic acid, aspartic acid, or arginine; monosaccharides, disaccharides, and other carbohydrates including cellulose or its derivatives, glucose, mannose, or dextrins; chelating agents such as EDTA; and sugar alcohols such as mannitol or sorbitol.

The polypeptide polymers to be used for therapeutic administration must be sterile. Sterility is readily accomplished by filtration through sterile filtration membranes (e.g., 0.2 micron membranes). The polypeptide polymer ordinarily will be stored in lyophilized form or as an aqueous solution if it is highly stable to thermal and oxidative denaturation. The pH of the polypeptide polymer preparations typically will be about from 6 to 8, although higher or lower pH values may also be appropriate in certain instances. It will be understood that use of certain of the foregoing excipients, carriers, or stabilizers will result in the formation of salts of the polypeptide polymer.

Therapeutic compositions containing the polypeptide polymer generally are placed into a container having a sterile access port, for example, an intravenous solution bag or vial having a stopper pierceable by a hypodermic injection needle.

Generally, where the disorder permits, one should formulate and dose the polypeptide polymer for site-specific delivery. This is convenient in the case of rheumatoid arthritis and inflammatory bowel disease. In the former case, the polypeptide polymer is formulated into a sterile sustained-release composition suitable for injection into the synovial fluid or implantation into the synovial lining or capsule. In one embodiment, it is administered into a diarthrodial joint. In the case of inflammatory bowel disease, the polypeptide polymer is formulated into suppositories with pharmaceutically acceptable oleaginous substances as is generally known in the art.

Sustained-release formulations will be selected from the classes of microcapaular particles and implantable articles. Liposomal encapsulation is not preferred for injection directly into the synovial cavity in rheumatoid arthritis because it entails the introduction of lipid into the joint. However, liposomal encapsulation is suitable for implantation of sustained release polypeptide polymer into the synovial capsule. For the treatment of rheumatoid arthritis using sustained-release polypeptide polymer compositions, the polymer is preferably incorporated into a biodegradable matrix or microcapsule. A suitable material for this purpose is a polylactide, although other polymers of poly-($\alpha$-hydroxycarboxylic acids), such as poly-D-($-$)-3-hydroxybutyric acid (EP 133,988A), can be used. Other biodegradable polymers include poly(lactones), poly(acetals), poly(orthoesters), or poly(orthocarbonates). The initial consideration here must be that the carrier itself, or its degradation products, is nontoxic in the target tissue and will not further aggravate the disease. This can be determined by routine screening in animal models of the target disorder or, if such models are unavailable, in normal animals.

For examples of sustained-release compositions, see U.S. Pat. No. 3,773,919, EP 58,481A, U.S. Pat. No. 3,887,699, EP 158,277A, Canadian Patent No. 1176565, U. Sidman et al., "Biopolymers" 22:547 [1983], and R. Langer et al., "Chem. Tech." 12:98 [1982].

The dosage to be employed is dependent upon the factors described above. As a general proposition, the polypeptide polymer is formulated and delivered to the target site or tissue at a dosage capable of establishing in the tissue a polypeptide polymer level greater than about 0.1 ng/cc up to a maximum dose that is efficacious but not unduly toxic. This intratissue concentration should be maintained if possible by continuous infusion, sustained release, or injection at empirically determined frequencies.

The preferred polypeptide polymer concentration in synovial fluid will be greater than about 0.1% of synovial fluid. Since RA synovial fluid can be present in amounts up to 50 ml, for example in a knee joint, the actual amount of polypeptide will depend upon its dilution into the synovial fluid as well as the empirically determined losses of the polypeptide polymer to endogenous proteases and leakage into the general circulation. Thus, it is best to evaluate the efficacy of the initial dosage protocol by withdrawing synovial fluid samples for the appropriate biological assay of the polypeptide during early stages of treatment to determine the proper dosage regimen.

The polypeptide polymers herein also are useful when administered by bronchial lavage or intravenous injection to patients with adult respiratory distress syndrome or septic shock.

It is within the scope hereof to combine the polypeptide polymer therapy with other novel or conventional therapies (e.g., growth factors such as EGF or TGF-$\alpha$) for the disorders in question. For example, in the case of rheumatoid arthritis, the polypeptide polymer therapy may be delivered in concert with other anti-inflammatory substances such as salicylate, nonsteroidal anti-inflammatory drugs, penicillamine, gold salts, TNF-α or TNF-β antagonists (described in U.S. Ser. No. 898,272 now abandoned, γ-interferon antagonists, and/or IL-1α/β antagonists. It is not necessary that such cotreatment drugs be included per se in the compositions of this invention, although this will be convenient where such drugs are proteinaceous such as in the case of antagonists to the activity of γ-interferon, TNF-α, IL-1α/β, and TNF-β (amino acid sequence variants or neutralizing antibodies).

Since the polypeptides herein are, in general, related to immunosuppressive proteins, they are also useful as imunogens to elicit antibodies capable of blocking the immunosuppressive activity associated with or caused by such immunosuppressive proteins, e.g., TGF-β. Examples of such activity include neoplastic or viral disorders. For making immunogenic peptides capable of eliciting antibodies to the immunosuppressive proteins, the polypeptides are typically not immunosuppressive, either because they are in monomeric form or because they are modified to be so. This modification can be performed by substituting one or more of the amino acids within the polypeptide polymer sequence to obtain non-immunosuppressive immunogenic forms of the polypeptides. The proper amino acids to be modified can be tested simply by making the substitution and testing the resultant polypeptide for the relevant activity.

The antibodies are obtained generally by injecting a mouse or other appropriate host animal with the relevant immunogen and then sacrificing the host animal. The resulting antibody-producing cells, taken, e.g., from its spleen or lymphoid tissue, are cultured so as to produce antibodies, which are then isolated.

Preferably, the antibodies herein are monoclonal antibodies, and more preferably human monoclonal antibodies. Monoclonal antibodies are generally obtained by the somatic cell hybridization procedure described by Milstein et al., *Nature*, 256: 495-497 (1975) and Koehler et al., *Eur. J. Immunol.*, 6:511-519 (1976). Basically, in this procedure the antibody-producing cells obtained as described above are fused with appropriate selectable cancer (myeloma) cells using a suitable fusogen such as polyethylene glycol to form a hybridoma. Preferred myeloma cells are those that fuse efficiently, support stable high-level expression of antibody by the selected antibody-producing cells, and are sensitive to a medium such as HAT medium. Examples of such myeloma cell lines are reurine myeloma lines such as those derived from MOPC-21 and MPC-11 mouse tumors available from the Salk Institute Cell Distribution Center in San Diego, California. The hybridomas thus prepared are washed to remove the fusogen and then seeded and grown in the selective media such as HAT to select only those hybridomas resistant to the medium and immortal.

The hybridomas thus selected are screened for production of individual antibodies directed against the specific antigens by, e.g., radioimmunoassay and/or enzyme immunoassay and are generally screened for affinity by similar techniques. Positive clones that produce antibodies that bind to different epitopes of a given immunosuppressive protein may be selected, in one technique by illustration only, by incubating the protein first with unlabeled antibody from one of the clones and next with labeled antibody from another clone to determine whether binding of the labeled antibody was blocked by binding of the unlabeled antibody.

It is noted that the labeled monoclonal antibodies of this invention may not only be whole immunoglobulin, but may also be monovalent or divalent fragments of the antibodies that bind to the antigen. Such fragments are suitably prepared by digesting the monoclonal antibody desired with suitable enzymes and isolating the desired fragment from the digest.

After the hybridomas are screened to isolate individual clones that secrete the antibodies having the desired specificity, reactivity, and affinity, if relevant, the clones may be subcloned by limiting dilution procedures and grown by known procedures. The monoclonal antibodies secreted by the subclones may be separated from the culture medium, ascites fluid, or serum by conventional immunoglobulin purification procedures such as, e.g., ammonium sulfate precipitation, gel electrophoresis, dialysis, DEAE cellulose chromatography, or affinity chromatography.

In another use aspect, the polypeptides herein are useful as immunogens to develop antibodies that can be coupled to appropriate surfaces for use in extracorporeal absorption to remove immunosuppressive proteins from body samples of patients afflicted with a disease associated with such proteins. Thus, one of the methods herein involves first identifying the responsible immunosuppressive protein, and then contacting the protein with an antibody that will neutralize the protein, preferably an immobilized antibody. For example, if the immunosuppressive protein is in the sera of the patient, the antibodies purified from the immunized hosts are suitably coupled to solid-phase matrices suitable for use in well known extracorporeal devices such as those currently used for plasmaphoresis.

The polypeptide polymers herein are also useful in developing diagnostic tests for the appearance of immunosuppressive proteins in the body samples of patients with disorders associated with such proteins. For example, antibodies to the immunosuppressive polypeptides are suitably screened for in the serum of patients at risk. Alternatively, using antibodies to such polypeptide polymers, one screens for immunosuppressive polypeptides in the circulation of at-risk patients. Detection of antibody as well as circulating antigen can be carried out through the use of well known solid-phase ELISA assays. (e.g., the forward, reverse, and simultaneous immunometric assays described in U.S. Pat. No. 4,376,110) or other immunoabsorption techniques, including Western blotting and radioimmunoprecipitation. The detection of circulating immunosuppressive activity would be followed by treatment to remove such circulating immunosuppressive proteins through immunoabsorptive techniques using the antibodies immobilized to supports.

In one particular embodiment, a solid phase support immobilizing unlabeled monoclonal antibodies directed against an immunosuppressive protein, the patient sample to be tested (preferably in a buffer), and the labeled monoclonal antibody directed against the protein in a buffer are mixed together and simultaneously incubated for about 30 minutes to about two hours at ambient temperature to 37° C. The resulting mixture is then washed with buffered solution appropriate for the particular ingredients being added. The washed mixture is then subjected to a detection means for the label, such as, e.g., ortho-phenylenediamine for horseradish peroxidase, phenolphthalein monophosphate for alkaline phosphatase, or p-nitrophenyl beta-D-galactopyranoside for beta-galactosidase to form a colored product that can be detected by its absorbance or visible color change, or fluorescence for the fluorescent labels. If a substrate is employed to detect an enzyme, a solution of the substrate is suitably added to the washed assay and the mixture then incubated for 15 to 30 minutes at 25°-37° C. Then a solution that terminates the enzyme action such as an acid may be added and the absorbance of the solution measured shortly thereafter to determine the amount of bound antigens.

In another assay procedure, the solid-phase support immobilizing the unlabeled antibody and the patient sample are mixed together, incubated as described above, and then aspirated. To the aspirated mixture is then added the labeled antibody and the resulting mixture is incubated as described above for the simultaneous assay. The mixture is then washed with appropriate buffer solution, and the washed mixture is then subjected to appropriate detection means for the label as described above.

For preparing labeled antibodies, any method may be employed, including those methods described by U.S. Pat. No. 3,940,475 (fluorimetry) and U.S. Pat. No. 3,645,090 (enzymes), Hunter et al., *Nature*, 144:945 (1962), David et al., *Biochemistry*, 13:1014–1021 (1974), Pain et al., *J. Immunol. Methods*, 40:219–230 (1981), and Nygren, *J. Histochem. and Cytochem.*, 30:407–412 (1982).

For preparing immobilized antibodies for physically extracting the immunosuppressive protein from the sample, any suitable method is employed. The support or carrier on which the antibodies are immobilized is generally essentially water-insoluble and may be any support known to be useful in immunometric assays, including supports in the form of, e.g., surfaces, particles, porous matrices, etc. Examples of commonly used supports include filter paper, Sephadex, polyvinylchloride, plastic beads or test tubes manufactured from polyethylene, polypropylene, polystyrene, and the like, agarose, crosslinked dextran, other polysaccharides, etc.

The method for conjugating the support to the antibodies, which may occur before or during the assay as desired, is achieved by chemically or physically binding the antibody to an essentially water-insoluble surface, matrix, or body. The method described in U.S. Pat. No. 3,645,852 or in Rotmans et al., *J. Immunol. Meth.*, 57:87–98 (1983) for conjugating a single antibody to a support is suitably employed.

Yet another use of the invention is in the treatment of periodontal disease, orthopedic implants, cutaneous burns, chronic wounds, ulcers, and non-union bone fractures. The polypeptide polymers herein are small and diffusible so that they can be easily released in a topical format in an effective amount to the desired site. The topical formulation includes administration by means of ointments, creams, lotions, gels, salves, skin patches, and bandages such as impregnated adhesive bandages. The topical formulations particularly preferred herein are creams, salves, skin patches, and bandages. "Effective amount" in this context is the amount necessary to accelerate wound healing in the animal over the rate that would occur without treatment.

If the polypeptide formulation is to be applied topically to the wound, it is preferable to use a viscous solution such as a gel rather than a non-viscous solution. This may be accomplished, for example, by mixing the solution of the polypeptide polymer with a gelling agent, such as a polysaccharide, preferably a water-soluble polysaccharide, such as, e.g., hyaluronic acid, starches, and cellulose derivatives, e.g., methylcellulose, hydroxyethyl cellulose, and carboxymethyl cellulose. The polysaccharide is generally present in a gel formulation in the range of 1–90% by weight of the gel, more preferably 1–20%. Examples of other suitable polysaccharides for this purpose, and a determination of the solubility of the polysaccharides, are found in EP 267,015, published May 11, 1988, the disclosure of which is incorporated herein by reference.

The invention will be more fully understood by reference to the following examples. They should not, however, be construed as limiting the scope of the invention. All literature citations are incorporated by reference.

EXAMPLE I

A. Polypeptides

A polypeptide chain of the sequence Cys-Val-Arg-Gln-Leu-Tyr-Ile-Asp-Phe-Arg-Lys-Asp-Leu-Gly-Trp-Lys was synthesized via solid-phase synthetic methodology in accordance with Barany, G. and Merrifield, R. B. in *The Peptides*, 2:1–284, Gross, E. and Meinhofer, J., Eds., (New York: Academic Press, 1980). The polypeptide was synthesized using N-t-butyloxycarbonyl protocols. The following side chain protection was used: Lys, o-chlorobenzyloxycarbonyl; Asp, cyclohexyl eater; Arg, tosyl; Tyr, 2,6-dichlorobenzyl; Gln, xanthyl; Cys, methylbenzyl. Cleavage from the resin and removal of all the protecting groups was accomplished by treatment with anhydrous liquid hydrogen fluoride in the presence of anisole and methylethylsulfide (20:3:3) at 0° C. for one hour.

Crude peptide was removed from the resin with 10% aqueous acetic acid and lyophilized. The peptide was purified via HPLC on Vydac C18 using a water-acetonitrile/0.1% trifluoroacetic acid (TFA) elution system. The polypeptide was lyophilized and then taken up in water at a concentration of 10 mg/ml. The pH was adjusted to 8.5 with ammonium hydroxide. The polypeptide immediately started to precipitate. Stirring continued for 12 hours. TFA was added to adjust the pH to 2.0 and the polypeptide was lyophilized and repurified by HPLC or was repurified by HPLC directly. This resulted in polypeptide free from excess salts.

The polypeptide so prepared was coupled to human serum albumin (HSA; Sigma, St. Louis, Mo.) using carbodiimide by the following method: the polypeptide (1.0 mN) and HSA (0.03 mN) were mixed in 0.1M 1-ethyl-3-(3-dimethylaminopropyl)carbodiimide HCl for ca. 10 hr. at 22° C. and pH 5.0. An equal volume of 1.0M glycine was added, and the mixture was rotated overnight at 4° C. and then extensively dialyzed against Hank's Balanced Salt Solution containing 10 mM HEPES buffer and adjusted to pH 7.2. HSA alone was processed in an identical manner and used as an additional control.

B. Assays and Results

1. Inhibition of Proliferation of Cultured Mink Lung Cells (FIG. 1)

The cell line Mu-1-Lv (ATCC CCL 64, Rockville, Md.), a mink lung epithelial-like cell, was used to detect TGF-$\beta$ activity. Mul-1-Lv cells maintained by weekly passage in vitro in CMEM consisting of Eagle's minimum essential medium supplemented with 0.1 mm non-essential amino acids, 2 mM L-glutamine, 1 MM sodium pyruvate (Gibco, Grand Island, N.Y.), and 10% heat-inactivated fetal bovine serum (FBC; HyClone Laboratoris, Logan, Utah) were placed into 96-well flat-bottom microtiter plates (10,000/well; Falcon 3075) at a final volume of 200 μl/well. The plates were incubated at 37° C.+5% $CO_2$ for 24 hours. During the last 4 hours of culture, 1 μCi of [3H]thymidine (20 μl/well, 5.0 Ci/mmol; Amersham Corp.) was added. After labeling, 100 μl/well of 10 x Trypsin-EDTA was added per well and the plates were incubated for an additional 15 min. at 37° C. Cells were harvested onto glass filters and counted in a liquid scintillation counter (IS 6800, Beckman, Fullerton, Calif.). Results (pg/ml of TGF-P) were calculated based on percent inhibition of thymidine incorporation compared with a rHuTGF-$\beta_1$ laboratory standard.

FIG. 1 shows the cpm incorporated as a function of the reciprocal of dilution for the TGF-$\beta$ peptide conjugated to HSA (black), the HSA control (slashes), and unconjugated TGF-$\beta$ peptide (checks). The activities of both the free polypeptide and the HSA-conjugated polypeptide were found to be comparable, i.e., low at the low dilution level and high at the high dilution levels.

2. Stimulation of $PGE_2$ Production From Fibroblasts (FIG. 2)

Three to four days before assay WI-38 human fibroblasts (from the American Type Culture Collection, Rockville, Md.) were seeded in 96-well flat-bottom plates. On the day of the assay IL-1 was diluted to 2 u/ml in assay medium (modified Eagle's medium with 10% fetal bovine serum, L-glutamine, and penicillin/streptomycin (Gibco, Grand Island, N.Y.)). Samples to be tested were diluted 1:1 with the IL-1. To each of duplicate wells of the WI-38 cells was added 100 μl of sample. The plates were incubated overnight at 37° C. with 5% carbon dioxide. Supernatant from each well was collected for assay of amount of PGE2 released. Thus, twenty μl of each supernatant was added to 80 μl of RIA assay buffer and the diluted supernatant was assayed for $PGE_2$ according to the directions of the supplier ($PGE_2$ RIA kit, DuPont NEN, cat. #NEK-020).

Figure 2:
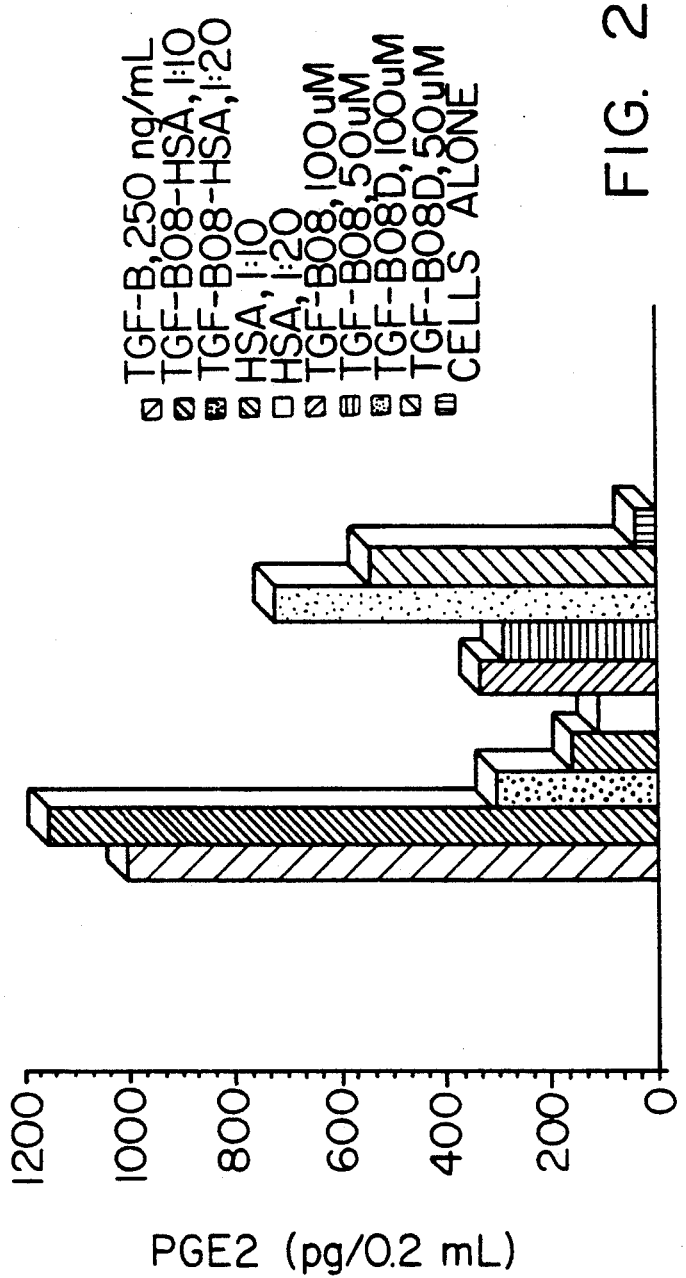
FIG. 2 represents bar graphs of the amount of PGE2 released by IL-1 treated human fibroblasts as a function of various TGF-β peptides, TGF-β1, HSA alone, and cells alone.

FIG. 2 illustrates the results for each sample, with the designations indicated as follows, from left to right in the graph in the figure: TGF-$\beta$, 250 ng/ml (solid bar), TGF-$\beta$ peptide conjugated to HSA diluted 1:10 (dark diagonal bar), TCF-$\beta$ peptide conjugated to HSA diluted 1:20 (light crosshatched bar), HSA alone diluted 1:10 (light diagonal bar), HSA diluted 1:20 (white bar), TGF-$\beta$ peptide, 100 μM (dark crosshatched bar), TGF-$\beta$ peptide, 50 μM (horizontally lined bar), TGF-$\beta$ peptide dimer, 100 μM (medium dotted bar). to TGF-$\beta$ peptide dimer, 50 μM (thin diagonal lines on white background bar), and cells alone as control (light dotted bar). The results show that the conjugated TGF-$\beta$ peptides and peptide dimers are the most active in this bioassay to stimulate $PGE_2$ production from fibroblasts. The HSA control and cells alone were inactive.

Figure 3:
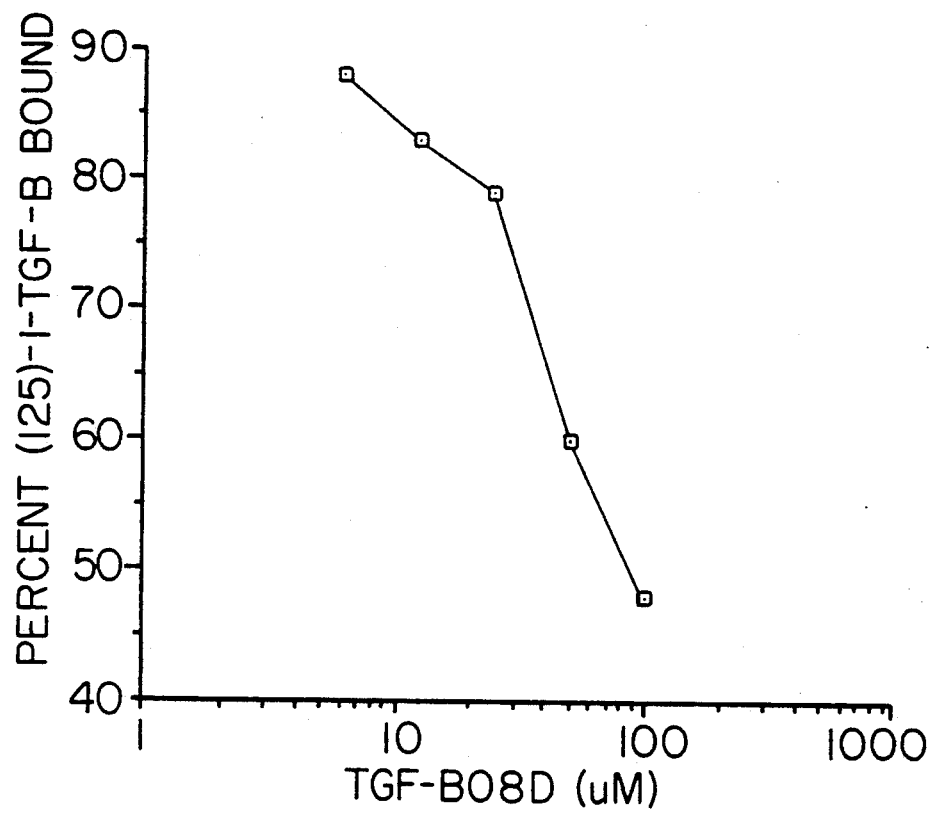
FIG. 3 represents a graph of the percent radiolabeled TGF-β1 bound to its receptors as a function of the concentration of TGF-β peptide dimer present.

3. TGF-$\beta$ Radioreceptor Binding Assay (FIG. 3)

The appropriate number of 24-well tissue culture plates were placed in an incubator. Frozen A549 (human lung carcinoma) cells obtained from the American Type Culture Collection, Rockville, Md. (low passage) were thawed, and the resultant near confluent A549 monolayers were treated with trypsin under standard conditions to wash the cells that adhered to the flasks. Then the flasks were rinsed with growth medium (prepared by adding to 50 ml calf serum an amount to constitute 1.0 liter of a medium prepared by mixing 10 ml L-glutamine, 200 mM or 100 x, sterile (Gibco), 10 ml sodium pyruvate, 100 mM or 100x, sterile (Gibco), and high glucose Dulbeccol's Modified Eagle Medium to 1.0 liter). The cells were pipetted up and down to obtain an even cell suspension. The cells were then counted.

A cell suspension was prepared by adding 1 ml of the cells to each well of all of the plates. Seeding density was 1.7-2.0 x $10^5$ cells/ml. The vessels containing the cell suspension were rinsed with growth medium and the rinse was discarded. A total of 1 ml of the growth medium was added to the wells of column 6 of plate #3. This was used as the cell-free blank.

The cell suspension was prepared using the growth medium and filling the remaining wells of each plate with 1 ml per cell. The cells were kept stirred while being added to the plate. The suspensions were incubated for 18-26 hours at 37° C. with 54 $CO_2$ to obtain 90-95% confluency. The media were aspirated from the cell plate. One ml of assay diluent was added to all the wells of the cell plate. Assay diluent van prepared by mixing 8.5 ml 5M NaCl, 0.1% v/v 10% bovine serum albumin (BSAY), prepared, if used for washing plates, by mixing BSA (Sigma RIA grade) at 100 g with deionized water to 1.0 liter or, if used for diluting standards, samples, and tracer, by mixing BSA ((Schwarz/Mann Biotech) at 100 g with deionized water to 1.0 liter, 25 ml of 1.0M HEPES, and sufficient assay medium to bring the total to 1.0 liter, assay medium being Ham's F-12 without GHT:low glucose Dulbeccol's Modified Eagle Medium without $NaHCO_3$, without glycine 50:50/0.1% bovine serum albumin/25 mK HEPES buffer/42.5 mM sodium chloride. Each plate was swirled by hand gently and the assay diluent was Immediately aspirated from the cell plate. The cell plates were covered and incubated at ambient temperature for 20 to 30 minutes.

Eleven 12×55 mm dilution tubes were labeled as follows:

| Label | Contents |
| --- | --- |
| NSB | NSB tube |
| REF | Reference (maximum binding) tube |
| ST1 | 25.0 ng/ml standard |
| ST2 | 12.5 ng/ml standard |
| ST3 | 6.25 ng/ml standard |
| ST4 | 3.12 ng/ml standard |
| ST5 | 1.56 ng/ml standard |
| ST6 | 0.78 ng/ml standard |
| ST7 | 0.39 ng/ml standard |
| ST8 | 0.195 ng/ml standard |
| BLK | Cell-free blank tube |

A total of 0.975 ml of assay diluent was added to tube ST1. To the remaining tubes was added 0.5 ml assay diluent. A total of 10 μl of recombinant full-length mature TGF-$\beta$ in 4mm HCl and 1% w/v BSA was pipetted into tube NSB. A different lot of full-length mature TGF-$\beta$ in 4mM HCl and 1% w/v BSA (standard stock) was diluted in accordance with the following schedule, where "standard stock I" is obtained by diluting the TGF-,6 standard stock 1:5 with assay diluent (i.e., 20 μl standard stock and 80 μl assay diluent):

| Standard | ng/ml | Standard to Add | Assay Diluent to Add |
|---|---|---|---|
| A | 25.0 | 25 μl standard stock I | 975 μl |
| B | 12.5 | 0.5 ml std A | 0.5 ml |
| C | 6.25 | 0.5 ml std B | 0.5 ml |
| D | 3.12 | 0.5 ml std C | 0.5 ml |
| E | 1.56 | 0.5 ml std D | 0.5 ml |
| F | 0.78 | 0.5 ml std E | 0.5 ml |
| G | 0.39 | 0.5 ml std F | 0.5 ml |
| H | 0.19 | 0.5 ml std G | 0.5 ml |

A total of 0.5 ml was removed and discarded from tube H. The TGF-$\beta$ peptide dimer was diluted similarly such that the final concentrations of TGF-$\beta$ dimer ranged from 6.25 to 100 μM.

The TGF-$\beta$ control stock (yet a different lot of recombinant full-length mature TGF-$\beta$ in 4 MM HCl and 1% w/v BSA) was diluted in accordance with the following schedule, with "control stock I" referring to dilution of the TGF-$\beta$ control stock 1:5 with the assay diluent)(i.e., 20 μl control stock and 80 μl assay diluent:

| Control | ng/ml | Control to Add | Assay Diluent to Add |
|---|---|---|---|
| A | 10 | 10 μl control stock I | 990 μl |
| B | 5 | 0.5 ml of A | 0.5 ml |
| C | 2.5 | 0.5 ml of B | 0.5 ml |
| D | 1.2 | 0.5 ml C3 of C | 0.5 ml |
| E | 0.6 | 0.5 ml C4 of D | 0.5 ml |
| F = blank | 0 | 0 | 0.5 ml |

A total of 0.5 ml was removed and discarded from tube E.

The tracer $^{125}$I was diluted in the assay diluent to 20,000 cpm/100 μl (at iodination) and 0.5 al of the diluted tracer was added to all tubes. The resulting samples were mixed gently. A total of 100 μl of the diluted tracer was pipetted into each of four counting tubes (12×75 mm polypropylene round-bottom tubes) for use as Total Count tubes. These tubes were set aside until calculation/assay analysis.

The assay diluent was aspirated from the cell plates. A total of 200 μl, in quadruplicate, of the NSB, REF, standard dilutions of TGF-$\beta$, TGF-$\beta$ controls, blank, and TGF-$\beta$ peptide standard dilutions were transferred from the dilution tubes to the appropriate wells of the cell plates. The plates were covered with plate sealers and incubated for 2 hours at ambient temperature, with gentle rocking on a rocker platform.

A total of 1 ml of tracer wash buffer (PBS/0.1% BSA prepared from 10 ml 10% BSA and PBS to a total of 1.0 liter) on ice was added to all wells, and all wells were aspirated. The steps of adding 1 ml of tracer wash buffer and aspirating were carried out three more times for a total of four 1-ml washes. All wells were aspirated completely; the plates were covered and set aside. A total of 0.75 ml solubilization buffer (10% glycerol/10% TritonX-100/25 mM HEPES, prepared by adding 200 ml 504 glycerol, 100 ml Triton X-100, 25 ml of 1.0M HEPES, and deionized water to reach a total of 1.0 liter) was added to each well. All plates were incubated for 30 min. at 37° C. on a plate rotator. The entire contents of each well was transferred into a counting tubs, and all tubes were counted on a gamma counter for 5 minutes each.

The sample concentration of TGF-$\beta$ was determined using a four-parameter logistic curve-fitting program with the data for the TGF-$\beta$ standard dilution samples, so that the percent labeled TGF-$\beta$ bound could be determined.

As shown in FIG. 3, the conjugated polypeptide was found to block the binding of radiolabeled TGF-$\beta$ to its receptor, and was increasingly effective at blocking with increasing concentrations.

Figure 4:
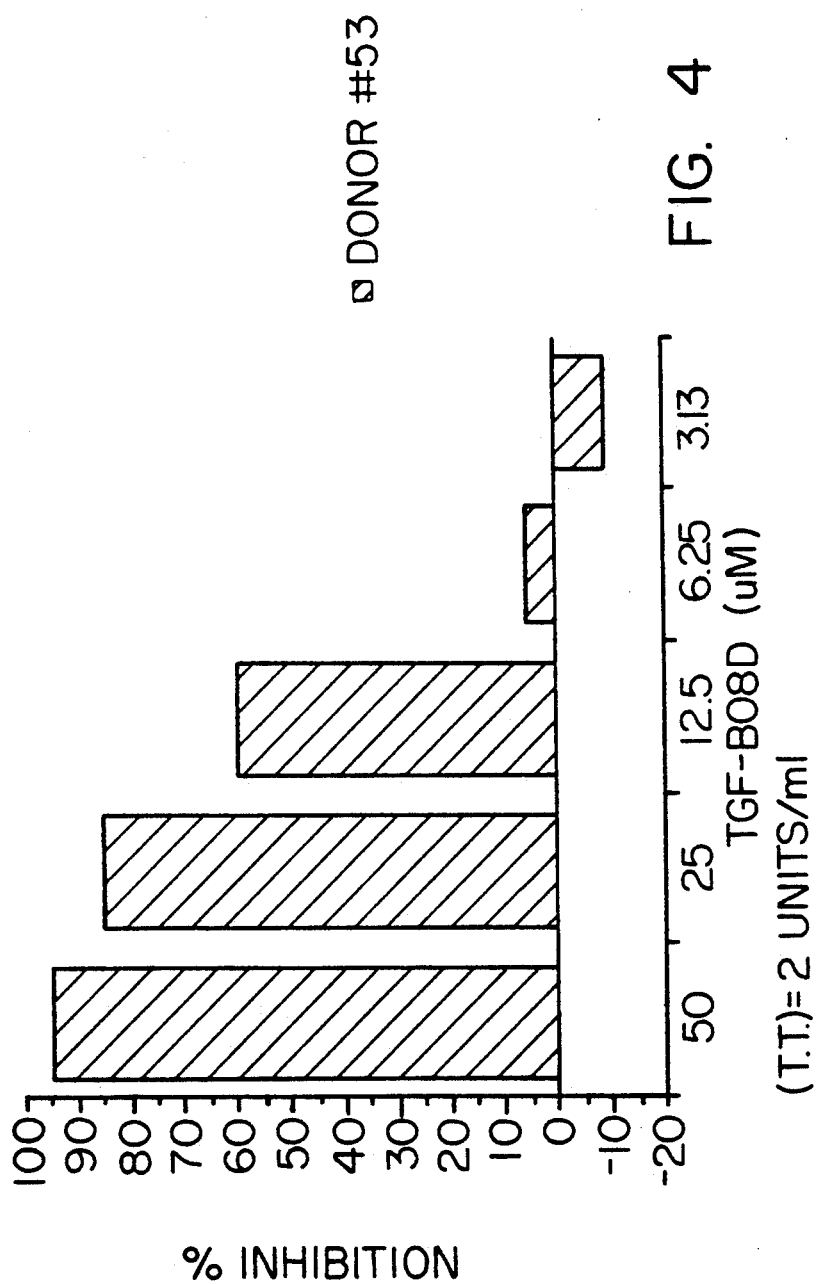
FIG. 4 represents a bar graph of percent inhibition of tetanus-toxoid-stimulated human lymphocyte proliferation versus concentration of synthetic 16-mer dimer herein.
Figure 5:
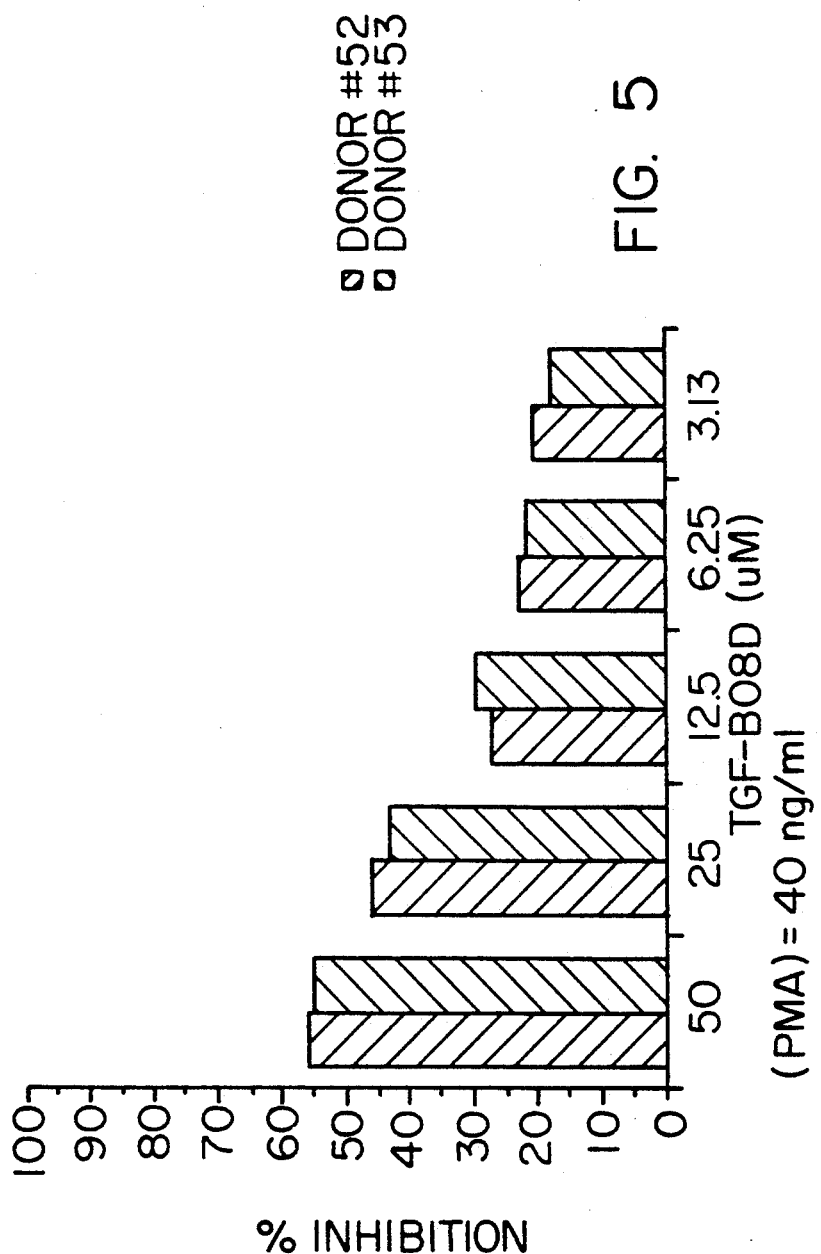
FIG. 5 represents a bar graph of percent inhibition of PMA-stimulated human lymphocyte proliferation versus concentration of synthetic 16-mer dimer herein, for two different donors (black and hatched).
Figure 6:
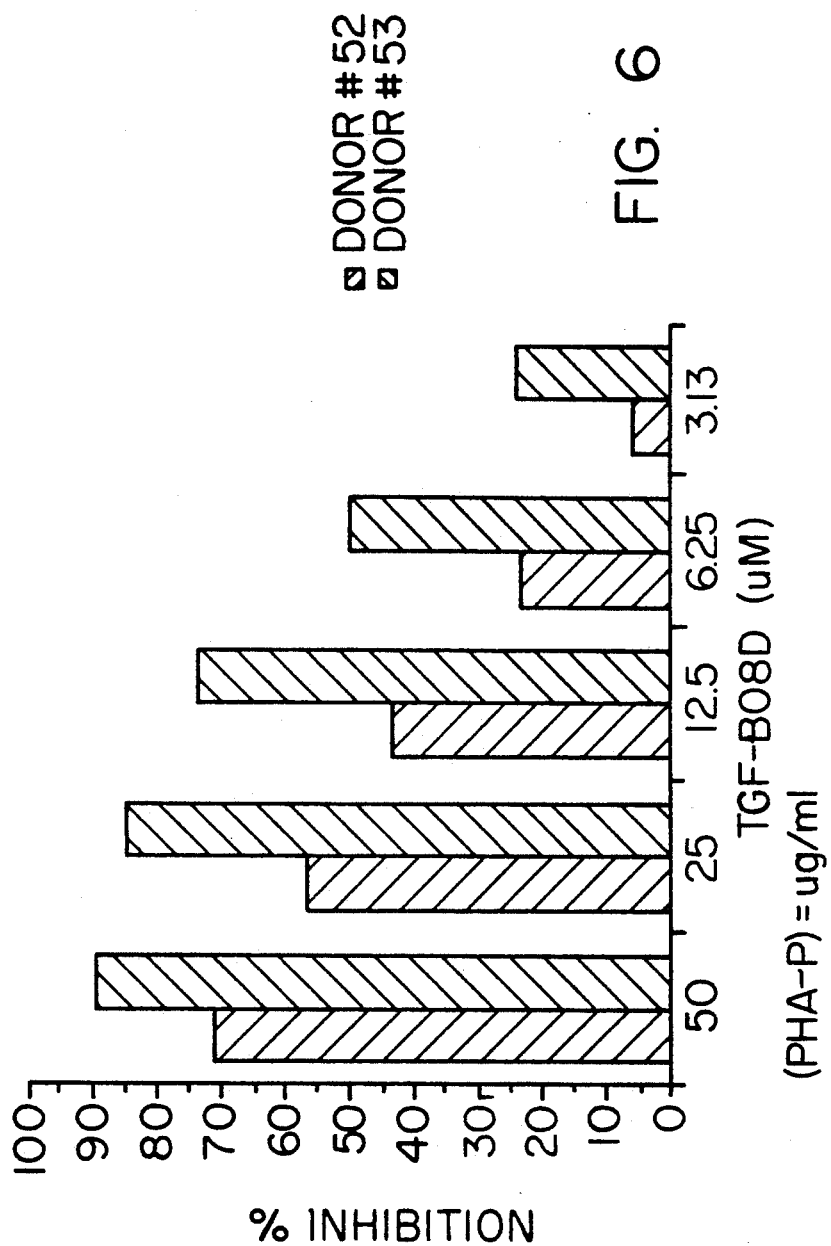
FIG. 6 represents a bar graph of percent inhibition of PHA-P-stimulated human lymphocyte proliferation versus concentration of synthetic 16-mer dimer herein, for the same two donors as shown in FIG. 5.

4. Inhibition of Proliferation of Human Lymphocytes in Response to Tetanus Toxoid (FIG. 4), PMA (FIG. 5), and PHA (FIG. 6)

The medium employed was complete RPMI-1640, i.e., RPMI-1640 (Gibco) supplemented with 10% human pooled AB serum (Hazelton Biologics Inc., Lenexa, Kans.), 100 μ/ml penicillin/100 μ/ml streptomycin, 2 mM L-glutamine (Gibco), 1 mM sodium pyruvate (Gibco), 1% MEM non-essential amino acids (Gibco, 100x), 25 mM HEPES (Gibco), and 14 Nutridoma (Boehringer Mannheim).

Heparinized venous blood (10 u/ml; bovine lung, Upjohn) was mixed with an equal volume of isotonic saline. Approximately 30 ml of the diluted blood was layered over 15 ml of lymphocyte separation medium (LSM, Organon Technika) in 50-m conical polypropylene centrifuge tubes (Falcon Plastics). The tubes were centrifuged for 40 min. at 400 x g at 22° C. The mononuclear cell layer at the plasma-LSM interface was carefully removed into a 50-ml conical tube to which at least an additional five volumes of ice-cold Hank's Balanced Salt Solution (RBSS, Gibco, 10 mK HEPES buffer, pH 7.4) was added. The cells were then washed three times with HBSS by centrifugation for 15 min. at 200 x g at 4° C. The cells were then resuspended in complete RPMI-1640 and both a total and differential cell count was performed. The concentration of cells was adjusted to $1 \times 10^6$ lymphocytes per ml.

To each of sextuplicate wells of a 96-well flat-bottom microtiter plate (Falcon Plastics) was added 100 μl of the cell suspension. Fifty μl of medium or medium containing the test article was added to the cells. An additional 50 μl of either medium alone or medium containing the appropriate mitogen (PHA-P, 1 μg/ml, Sigma; PMA, 40 ng/ml, Calbiochem; tetanus toxoid, 2 LF units/ml, State Lab Inst., Jamaica Plain, Mass.) was added to the appropriate wells and the plates were incubated for three days (PMA and PHA) or six days (tetanus toxoid) at 37° C. in humidified 5% $CO_2$. For the final six hours of incubation, an additional 50 μl of medium containing 0.5 μCi of 3H-thymidine (Amersham, 40-60 Ci/mmol) was added and the cultured cells were harvested onto glass-fiber filter discs using an automated multiple sample harvester. The filter discs were dried and suspended in 2 ml of liquid scintillation cocktail (Econofluor, New England Nuclear) in miniscintillation vials and incorporated radioactivity was determined by liquid scintillation spectrophotometry. Data were expressed as mean counts per min. of the quadruplicate samples, where the cpm of the media control was subtracted from the cpm of the stimulated sample.

The synthetic TGF-$\beta$ polypeptide herein was found to inhibit the proliferation of human lymphocytes in response to tetanus toxoid (FIG. 4), PMA (FIG. 5), and PHA-P (FIG. 6), in a dosedependent manner. Mature, full-length TGF-$\beta$1 also exhibits this dose-dependent effect, suggesting that the synthetic polypeptide represents all or part of the active site of TGF-$\beta$1.

5. Inhibition of Human Monocyte Chemotactic Response (FIG. 7)

Human mononuclear cells were isolated from heparinized venous blood of normal human volunteers. The heparinized venous blood was mixed 1:1 with 3% dextran (T500 Pharmacia, Piscataway, N.J.) and sedimented at room temperature for 30 minutes. A mononuclear cell band was isolated on lymphocyte separation medium (Organon Teknika Corp., Durham, N.C.) and washed twice in saline. Cells were counted with a hemacytometer and the monocyte concentration was determined by staining for myeloperoxidase. Cells were then resuspended to $7.5 \times 10^5$ monocytex/ml in RPMI-1640 medium with L-glutamine (Hazelton Biologics Inc.), containing 25 mM HEPES and 0.5% bovine serum albumin (BSA).

Inhibition of chemotaxis was assayed in a 48-well microchemotaxis chamber (Neuro Probe, Inc., Cabin John, Md.). Monocytes were preincubated with medium or the TGF-β polypeptide dimer diluted in medium at room temperature for 30 minutes. (All dilutions were made in RPMI-1640 medium with L-glutamine containing 25 mM HEPES and 0.5% BSA.) The mixture was then added to the top compartment of the chemotaxis chamber. The lower compartment contained the chemoattractant N-formyl-methionyl-leucyl-phanylalanine (FMLP, in separate experiments at $10^{-8}$ and $10^{-9}$M) (Sigma, St. Louis, Mo.). A polycarbonate filter (5.0 μm pore size, Millipore Corp., Bedford, Mass.) separated the compartments. Chambers were incubated for 90 minutes at 37° C. After incubation, the chambers were disassembled quickly and the filters were stained using Diff-Quik (American Scientific Products, McGaw Park, Ill.). The filters were then mounted on slides using immersion oil. Slides were read by counting the number of cells that had migrated through the filter in five-40x fields per well.

Figure 7:
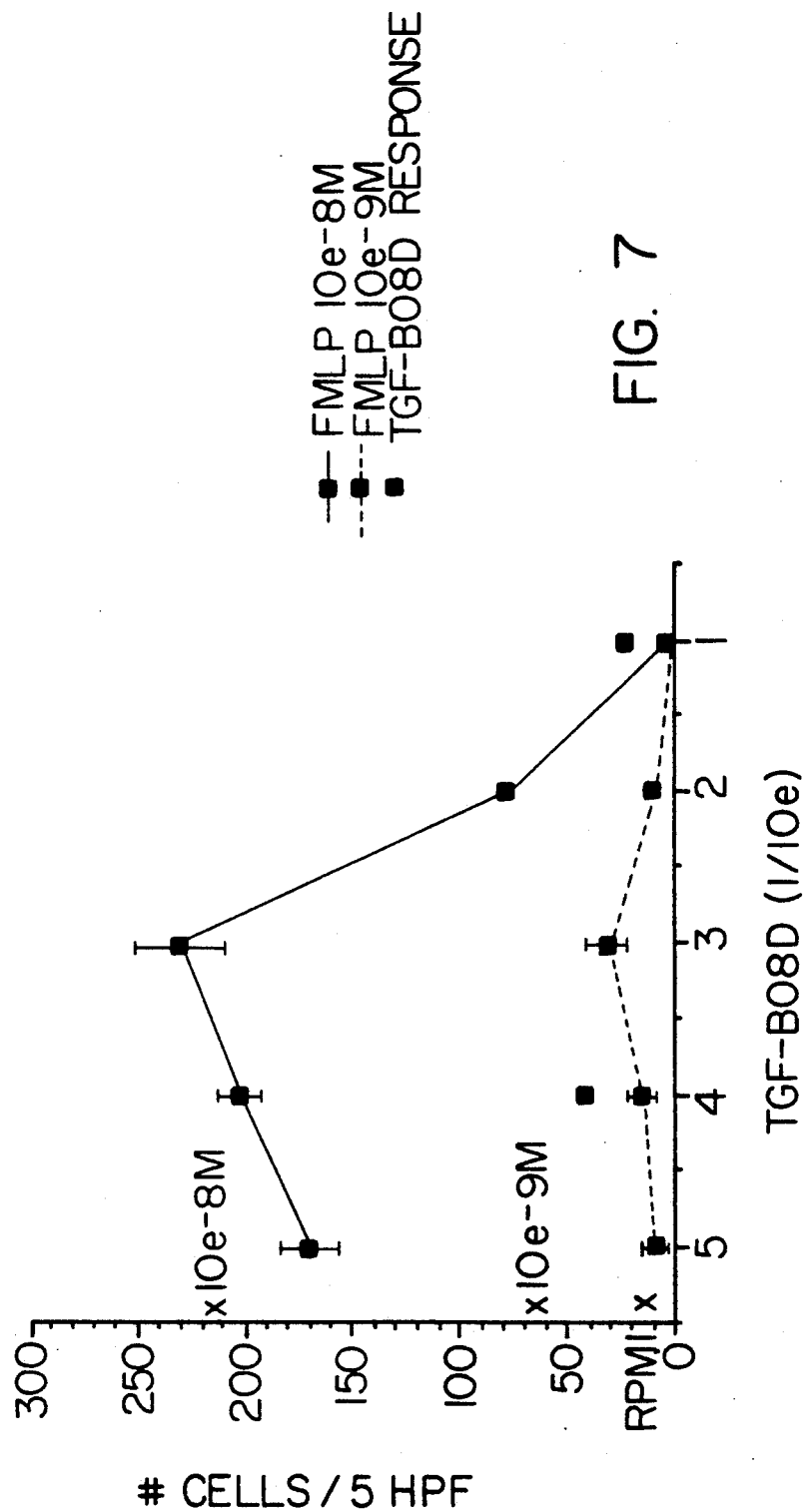
FIG. 7 represents a graph of the number of monocytes migrating as a function of 16-mer dimer concentration in response to chemotaxis by two different concentrations of FMLP (squares with lines are FMLP $10^{-8}$M; circles with lines are FMLP $10^{-9}$M; and squares without lines are the TGF-β peptide response).

The number of monocytes as a function of polypeptide concentration is plotted in FIG. 7 for FMLP at the two concentrations and for the response of the polypeptide. The results show that the peptide inhibits monocyte chemotaxis in response to FMLP, similarly to what is seen for FMLP at concentrations of $10^{-9}$M.

EXAMPLE III

Groups of ten DBA/IJ male mice (Jackson Laboratories) each are injected subcutaneously with 100 μg chicken collagen Type II in complete Freund's adjuvant (CFA) on day 0. The mice are boosted with 100 μg chicken collagen Type II intraperitoneally in CFA on day 28. The mice are either untreated with the HSA-conjugated polypeptide of Example I or treated intravenously from days 0-4 with 5 μg of the conjugated polypeptide or from days 7-11, or 14-18, or 28-32, or various combinations thereof with 2 μg of the conjugated polypeptide. The incidence (number of joints affected and severity of involvement) of collagen Type II-induced arthritis on days 37, 42, 49, 55, and 62 is measured on a scale of 0 to 4+, with 4+ representing significantly increased joint swelling. The incidence of arthritis in every treatment with the conjugated polypeptide is less than with the control, when compared on the same day, except the 2 μg treatment at days 7-11, which shows similar results to the control at days 49 and 55.

What is claimed is:

1. A process for obtaining a polypeptide that inhibits the in vitro proliferation of a cultured established mink lung cell line CCL 64 or in nitro proliferation of human lymphocytes to an antigen or a mitogen comprising crosslinking a monomeric polypeptide at one of its termini with at least one polypeptide chain homologous to the polypeptide, so as to form a polymer of the monomeric polypeptide, wherein the monomeric polypeptide comprises an amino acid sequence of the formula:

X-A-Arg-B-Leu-Tyr-Ile-Asp-Phe-H-I-Asp-Leu-Gly-Trp-Lys, wherein;
X is Cys or a crosslinker moiety of a polypeptide that has at its C-terminus a Cys, and that, if greater than 15 residues, does not have the sequence of mature or precursor TGF-β at a homologous location in the mature or precursor TGF-β molecule;
A is Val or Leu;
B is Pro or Gln;
H is Arg or Lys; and
I is Lys, Arg, or Gln; or a physiologically acceptable salt or ester thereof; provided, however, that the polypeptide excludes (a) a full-length mature TFG-β molecule or precursor TGF-β molecule or deletion variants of mature or precursor TGF-β molecules in which from about 1 to 10 amino acid residues have been deleted, (b) a polypeptide of the sequence: Cys-Val-Arg-Gln-Leu-Tyr-Ile-Asp-Phe-Arg-Lys-Asp-Leu-Gly-Trp-Lys, and (c) a polypeptide of the sequence: Arg-Asn-Leu-Glu-Glu-Asn-Cys-Cys-Val-Arg-Pro-Leu-Tyr-Ile-Asp-Phe-Arg-Gln-Asp-Leu.

2. The process of claim 1 wherein the crosslinking is through disulfide bonds and the polymer is a dimer.

3. The process of claim 1 wherein the polymer is recovered.

4. The process of claim 1 wherein the homologous polypeptide chain is at least 90% homologous to the monomeric polypeptide.

5. The process of claim 1 wherein the homologous polypeptide chain is 100% homologous to the monomeric polypeptide and is dimerized.

6. The process of claim 1 wherein the polypeptide comprises an amino acid sequence of the formula:

Cys-A-Arg-B-Leu-Tyr-Ile-Asp-Phe-H-I-Asp-Leu-Gly-Trp-Lys wherein:
A is Val or Leu;
B is Pro or Gln;
H is Arg or Lys; and
I is Lys, Arg, or Gln.

7. The process of claim 6 wherein the polypeptide comprises an amino acid sequence of the formula:

Cys-Val-Arg-B-Leu-Tyr-Ile-Asp-Phe-Arg-I-Asp-Leu-Gly-Trp-Lys wherein:
B is Pro or Gln; and
I is Lys or Gln.

8. The process of claim 7 wherein B is Gln and I is Lys.

9. The process of claim 7 wherein B is Pro and I is Gln.

10. The process of claim 7 wherein the polypeptide has an amino acid sequence of the formula:

Cys-Leu-Arg-Pro-Leu-Tyr-Ile-Asp-Phe-Lys-Arg-Asp-Leu-Gly-Trp-Lys.

* * * * *